US010975359B2

(12) United States Patent
Gruber et al.

(10) Patent No.: US 10,975,359 B2
(45) Date of Patent: Apr. 13, 2021

(54) RETARGETING OF VIRUSES OR VLPS

(71) Applicant: Deutsches Primatenzentrum GmbH Leibniz-Institut für Primatenforschung, Göttingen (DE)

(72) Inventors: Jens Gruber, Göttingen (DE); Stefan Schneider, Göttingen (DE); Ellen Eckermann-Felkl, Duderstadt (DE); Alina Mosblech, Göttingen (DE); Arnd Steuernagel, Göttingen (DE); Dennis Wegener, Schenefeld (DE); Julian Plaga, Hamburg (DE)

(73) Assignee: Deutsches Primatenzentrum GmbH Leibniz-Institut für Primatenforschung, Göttingen (DE)

(*) Notice: Subject to any disclaimer, the term of this patent is extended or adjusted under 35 U.S.C. 154(b) by 0 days.

(21) Appl. No.: 16/482,771

(22) PCT Filed: Feb. 1, 2018

(86) PCT No.: PCT/EP2018/052523
§ 371 (c)(1),
(2) Date: Aug. 1, 2019

(87) PCT Pub. No.: WO2018/141849
PCT Pub. Date: Aug. 9, 2018

(65) Prior Publication Data
US 2019/0352617 A1 Nov. 21, 2019

(30) Foreign Application Priority Data
Feb. 2, 2017 (EP) .................................. 17154380

(51) Int. Cl.
*C12N 7/00* (2006.01)
*A61K 47/68* (2017.01)
(Continued)

(52) U.S. Cl.
CPC ................ *C12N 7/00* (2013.01); *A61K 47/68* (2017.08); *A61K 47/6901* (2017.08);
(Continued)

(58) Field of Classification Search
None
See application file for complete search history.

(56) References Cited

FOREIGN PATENT DOCUMENTS

| EP | 1270586 A2 | 1/2003 |
|---|---|---|
| WO | WO-2009/036933 A2 | 3/2009 |
| WO | WO-2016/091375 A1 | 6/2016 |

OTHER PUBLICATIONS

Varki, "Chapter 14: Sialic Acids,", Essentials of Glycobiology, 2nd edition, Cold Spring Harbor (NY); Cold Spring Harbor Laboratory Press (Year: 2009).*

(Continued)

*Primary Examiner* — M Franco G Salvoza
(74) *Attorney, Agent, or Firm* — Foley Hoag LLP

(57) ABSTRACT

The present invention relates to a method of producing a polyomavirus or polyomavirus-derived virus-like particle (vlp) carrying on its surface at least one targeting molecule that binds to a cell of interest. Furthermore, the present invention relates to a composition comprising such a polyomavirus or polyomavirus-derived vlp and to the use of the polyomavirus or polyomavirus-derived vlp of the invention or the composition of the invention for use as a medicament. The present invention further relates to a kit comprising the polyomavirus or polyomavirus-derived vlp or the composition of the invention.

Figure 1:
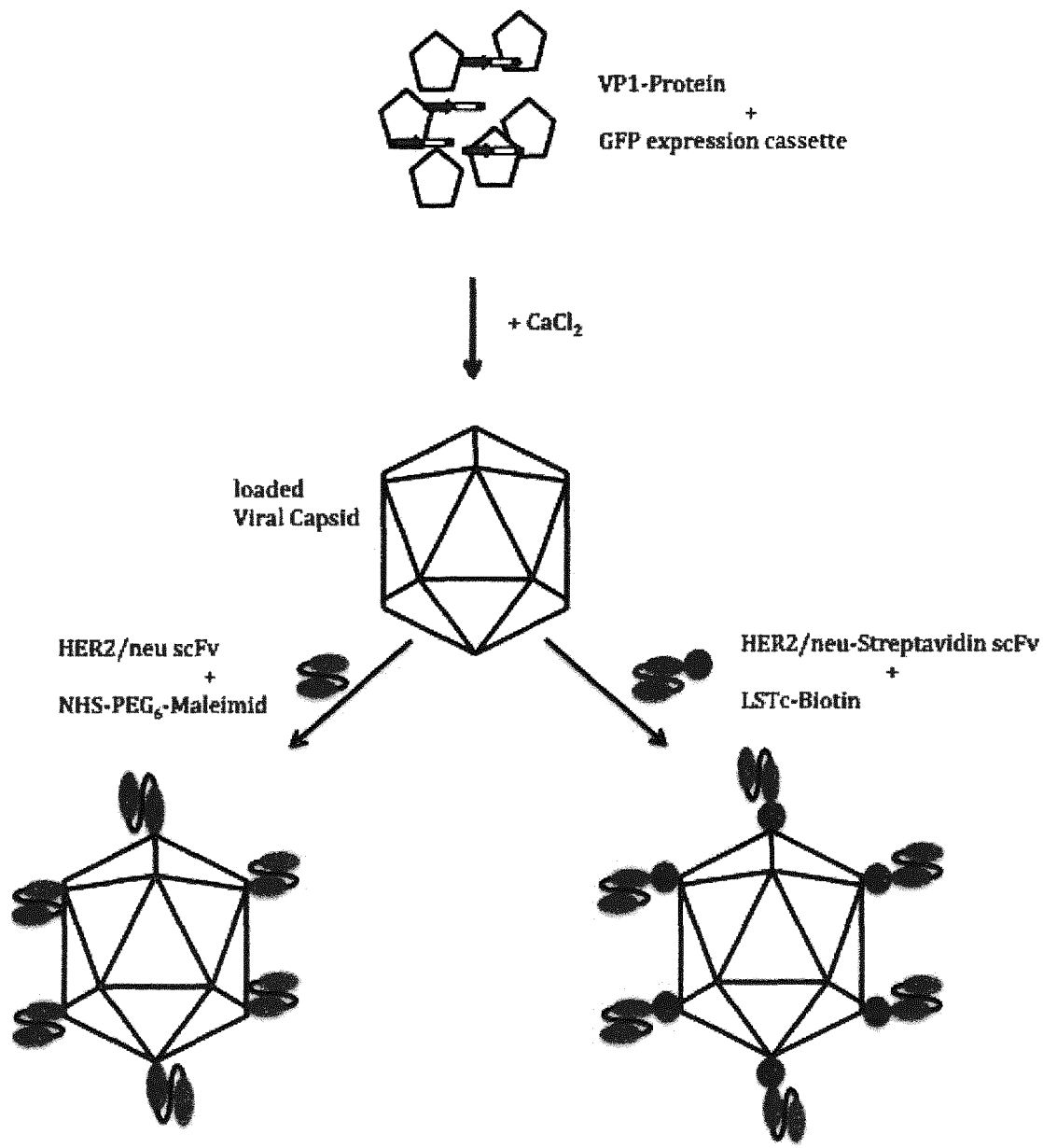

15 Claims, 10 Drawing Sheets
Specification includes a Sequence Listing.

(51) Int. Cl.
 *A61K 47/69* (2017.01)
 *C07K 16/32* (2006.01)
(52) U.S. Cl.
 CPC .... *C07K 16/32* (2013.01); *C12N 2710/22022* (2013.01); *C12N 2710/22023* (2013.01); *C12N 2710/22051* (2013.01)

(56) References Cited

OTHER PUBLICATIONS

Neu et al., "A Structure-Guided Mutation in the Major Capsid Protein Retargets BK Polyomavirus," PLoS Pathog 9(10): e1003688 (Year: 2013).*
Maginnis et al., "Progressive Multifocal Leukoencephalopathy-Associated Mutations in the JC Polyomavirus Capsid Disrupt Lactoseries Tetrasaccharide C Binding," mBIO 4(3): e00347-13 (Year: 2013).*
Neu et al., "Structure-Function Analysis of the Human JC Polyomavirus Establishes the LSTc Pentasaccharide as a Functional Receptor Motif," Cell Host & Microbe 8: 309-319 (Year: 2010).*
Kitai et al., "Cell selective targeting of a simian virus 40 virus-like particle nojugated to epidermal growth factor," Journal of Biotechnology 155: 251-256 (Year: 2011).*
Gleiter et al., "Coupling of antibodies via protein Z on modified polyoma virus-like particles," Protein Science 10: 434-444 (Year: 2001).*
O'Hara et al., "Glycan recognition by polyomaviruses," Current Opinion in Virology 7: 73-78 (Year: 2014).*
Deng et al., "Recombinant VLP-Z of JC Polyomavirus: A Novel Vector for Targeting Gene Delivery," Intervirol, 58(6):363-368 (2016).
International Search Report and Written Opinion for International Application No. PCT/EP2018/052523 dated Apr. 9, 2018.
Komagome et al., "Oligosaccharides as Receptors for JC Virus," Journal of Virology, 76(24):12992-13000 (2002).
O'Hara et al., "Glycan receptors of the Polymaviridae: structure, function, and pathogenesis," Current Opinion in Virology, 7:73-78 (2014).
Teunissen et al., "Production and biomedical applications of virus-like particles derived from polyomaviruses," Journal of Controlled Release, 172(1):305-321 (2013).

* cited by examiner b)

SEQUENCE LISTING

```
<160> NUMBER OF SEQ ID NOS: 32

<210> SEQ ID NO 1
<211> LENGTH: 1065
<212> TYPE: DNA
<213> ORGANISM: JC polyomavirus
<220> FEATURE:
<223> OTHER INFORMATION: VP1 capsid protein coding sequence

<400> SEQUENCE: 1 atggcccaa caaaagaaa aggagaaagg aaggacccg tgcaagttcc aaaacttctt      60
ataagaggag gagtagaagt tctagaagtt aaaactgggg ttgactcaat tacagaggta    120
gaatgctttt taactccaga aatgggtgac ccagatgagc atcttagggg ttttagtaag    180
tcaatatcta tatcagatac atttgaaagt gactccccaa ataggacat gcttccttgt    240 tacagtgtgg ccagaattcc actacccaat ctaaatgagg atctaacctg tggaaatata    300
ctcatgtggg aggctgtgac cttaaaaact gaggttatag gggtgacaag tttgatgaat    360
gtgcactcta atgggcaagc aactcatgac aatggtgcag ggaagccagt gcagggcacc    420
agctttcatt tttttctgt tggggggag gctttagaat tacagggggt gcttttttaat    480 tacagaacaa agtacccaga tggaacaatt tttccaaaga atgccacagt gcaatctcaa    540
gtcatgaaca cagagcacaa ggcgtaccta gataagaaca aagcatatcc tgttgaatgt    600
tgggttcctg atcccaccag aaatgaaaac acaagatatt ttgggacact aacaggagga    660
gaaaatgttc ctccagttct tcatataaca aacactgcca caacagtgtt gcttgatgaa    720
tttggtgttg ggccactttg caaaggtgac aacttatact tgtcagctgt tgatgtctgt    780
ggcatgttta caaacaggtc tggttcccag cagtggagag gactctccag atattttaag    840
gtgcagctaa ggaaaaggag ggttaaaaac ccctacccaa tttctttcct tcttactgat    900
ttaattaaca gaaggactcc tagagttgat gggcagccta tgtatggcat ggatgctcaa    960
gtagaggagg ttagagtttt tgagggaaca gaggagcttc caggggaccc agacatgatg   1020
```

```
agatacgttg acaaatatgg acagttgcag acaaaaatgc tgtaa                    1065
```

<210> SEQ ID NO 2
<211> LENGTH: 354
<212> TYPE: PRT
<213> ORGANISM: JC polyomavirus
<220> FEATURE:
<223> OTHER INFORMATION: Major capsid protein VP1

<400> SEQUENCE: 2

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Leu Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335

Pro Asp Met Met Arg Tyr Val Asp Lys Tyr Gly Gln Leu Gln Thr Lys
            340                 345                 350

Met Leu
```

<210> SEQ ID NO 3
<211> LENGTH: 1089
<212> TYPE: DNA
<213> ORGANISM: Artificial Sequence
<220> FEATURE:
<223> OTHER INFORMATION: Polyoma VP1-Mut2

<400> SEQUENCE: 3

```
atggccccaa caaaaagaaa aggagaatgt ccaggggcag ctcccaaaaa accaaaggac      60
cccgtgcaag ttccaaaact tcttataaga ggaggagtag aagttctaga agttaaaact     120
ggggttgact caattacaga ggtagaatgc ttttaactc cagaaatggg tgacccagat     180
gagcatctta ggggttttag taagtcaatt tctatatcag atacatttga agtgactcc     240
ccaaataagg acatgcttcc ttgttacagt gtggccagaa ttccactacc caatctaaat     300
gaggatctaa cctgtggaaa tatactaatg tgggaggctg tgaccttaaa aactgaggtt     360
ttaggggtga caactttgat gaatgtgcac tctaatggtc aagcaactca tgacaatggt     420
gcaggaaagc cagtgcaggg caccagcttt cattttttt ctgttggggg ggaggcttta     480
gaattacagg gggtggtttt taactacaga acaaagtacc cagatggaac aatttttcca     540
aagaatgcaa cagtgcaatc tcaagtaatg aacacagagc acaaggcgta cctagataag     600
aacaaagcat atcctgttga atgttgggtt cctgatccca ccagaaatga aaacacaaga     660
tattttggga cactaacagg aggagaaaat gttcctccag ttcttcatat aacaaacact     720
gccacaacag tgctgcttga tgaatttggt gttgggccac tttgcaaagg tgacaacttg     780
tatttgtcag ctgttgatgt tgtggaatg tttactaaca gatctggtac ccagcagtgg     840
agaggactgt ccagatattt taaggttcag ctgagaaaaa ggagggttaa aaacccctac     900
ccaatttctt tccttcttac tgatttgatt aacagaagga cccctagagt tgatgggcag     960
cctatgtatg gtatggatgc tcaggtagag gaggttagag tttttgaggg gacagaggaa    1020
cttccagggg acccagacat gatgagatat gttgacagat atggacagtt gcaaacaaag    1080
atgctgtaa                                                          1089
```

<210> SEQ ID NO 4
<211> LENGTH: 362
<212> TYPE: PRT
<213> ORGANISM: Artificial Sequence
<220> FEATURE:
<223> OTHER INFORMATION: VP1-Mut2

<400> SEQUENCE: 4

Met Ala Pro Thr Lys Arg Lys Gly Glu Cys Pro Gly Ala Ala Pro Lys
1               5                   10                  15

Lys Pro Lys Asp Pro Val Gln Val Pro Lys Leu Leu Ile Arg Gly Gly
            20                  25                  30

Val Glu Val Leu Glu Val Lys Thr Gly Val Asp Ser Ile Thr Glu Val
        35                  40                  45

Glu Cys Phe Leu Thr Pro Glu Met Gly Asp Pro Asp Glu His Leu Arg
    50                  55                  60

Gly Phe Ser Lys Ser Ile Ser Ile Ser Asp Thr Phe Glu Ser Asp Ser
65                  70                  75                  80

Pro Asn Lys Asp Met Leu Pro Cys Tyr Ser Val Ala Arg Ile Pro Leu
                85                  90                  95

Pro Asn Leu Asn Glu Asp Leu Thr Cys Gly Asn Ile Leu Met Trp Glu
            100                 105                 110

```
Ala Val Thr Leu Lys Thr Glu Val Leu Gly Val Thr Leu Met Asn
        115                 120                 125

Val His Ser Asn Gly Gln Ala Thr His Asp Asn Gly Ala Gly Lys Pro
    130                 135                 140

Val Gln Gly Thr Ser Phe His Phe Phe Ser Val Gly Gly Glu Ala Leu
145                 150                 155                 160

Glu Leu Gln Gly Val Val Phe Asn Tyr Arg Thr Lys Tyr Pro Asp Gly
                165                 170                 175

Thr Ile Phe Pro Lys Asn Ala Thr Val Gln Ser Gln Val Met Asn Thr
            180                 185                 190

Glu His Lys Ala Tyr Leu Asp Lys Asn Lys Ala Tyr Pro Val Glu Cys
        195                 200                 205

Trp Val Pro Asp Pro Thr Arg Asn Glu Asn Thr Arg Tyr Phe Gly Thr
    210                 215                 220

Leu Thr Gly Gly Glu Asn Val Pro Pro Val Leu His Ile Thr Asn Thr
225                 230                 235                 240

Ala Thr Thr Val Leu Leu Asp Glu Phe Gly Val Gly Pro Leu Cys Lys
                245                 250                 255

Gly Asp Asn Leu Tyr Leu Ser Ala Val Asp Val Cys Gly Met Phe Thr
            260                 265                 270

Asn Arg Ser Gly Thr Gln Gln Trp Arg Gly Leu Ser Arg Tyr Phe Lys
        275                 280                 285

Val Gln Leu Arg Lys Arg Val Lys Asn Pro Tyr Pro Ile Ser Phe
    290                 295                 300

Leu Leu Thr Asp Leu Ile Asn Arg Arg Thr Pro Arg Val Asp Gly Gln
305                 310                 315                 320

Pro Met Tyr Gly Met Asp Ala Gln Val Glu Glu Val Arg Val Phe Glu
                325                 330                 335

Gly Thr Glu Glu Leu Pro Gly Asp Pro Asp Met Met Arg Tyr Val Asp
            340                 345                 350

Arg Tyr Gly Gln Leu Gln Thr Lys Met Leu
        355                 360

<210> SEQ ID NO 5
<211> LENGTH: 6
<212> TYPE: PRT
<213> ORGANISM: Artificial Sequence
<220> FEATURE:
<223> OTHER INFORMATION: Nuclear localization signal

<400> SEQUENCE: 5

Cys Pro Gly Ala Ala Pro
1               5

<210> SEQ ID NO 6
<211> LENGTH: 11
<212> TYPE: PRT
<213> ORGANISM: Artificial Sequence
<220> FEATURE:
<223> OTHER INFORMATION: substance-P

<400> SEQUENCE: 6

Arg Pro Lys Pro Gln Gln Phe Phe Gly Leu Met
1               5                   10

<210> SEQ ID NO 7
<211> LENGTH: 7
<212> TYPE: PRT
```

```
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 7

Gln Glu Ile Asn Ser Ser Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 8

Ser His Pro Arg Leu Ser Ala
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 9

Ser Met Pro Asn Pro Met Val
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 10

Gly Leu Gln Gln Val Leu Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 11

His Glu Leu Ser Val Leu Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 12

Tyr Ala Pro Gln Arg Leu Pro
1               5
```

<210> SEQ ID NO 13
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 13

Thr Pro Arg Thr Leu Pro Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 14

Ala Pro Val His Ser Ser Ile
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 15

Ala Pro Pro His Ala Leu Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 16

Thr Phe Ser Asn Arg Phe Ile
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 17

Val Val Pro Thr Pro Pro Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Toll Like Receptor-4 (TLR-4) Agonist
      Peptide

<400> SEQUENCE: 18

Glu Leu Ala Pro Asp Ser Pro
1               5

<210> SEQ ID NO 19
<211> LENGTH: 25
<212> TYPE: DNA
<213> ORGANISM: Artificial Sequence
<220> FEATURE:
<223> OTHER INFORMATION: forward primer for CAG-GFP expression construct

<400> SEQUENCE: 19
gatcgtacca ttgacgtcaa taatg                                   25

<210> SEQ ID NO 20
<211> LENGTH: 20
<212> TYPE: DNA
<213> ORGANISM: Artificial Sequence
<220> FEATURE:
<223> OTHER INFORMATION: reverse primer for CAG-GFP expression construct

<400> SEQUENCE: 20 tctcccctg aacctgaaac                                          20

<210> SEQ ID NO 21
<211> LENGTH: 17
<212> TYPE: DNA
<213> ORGANISM: Artificial Sequence
<220> FEATURE:
<223> OTHER INFORMATION: forward primer for woodchuck hepatitis virus
      posttranslational regulatory element (WPRE)

<400> SEQUENCE: 21
tcgataccgt cgacccg                                            17

<210> SEQ ID NO 22
<211> LENGTH: 26
<212> TYPE: DNA
<213> ORGANISM: Artificial Sequence
<220> FEATURE:
<223> OTHER INFORMATION: reverse primer for woodchuck hepatitis virus
      posttranslational regulatory element (WPRE)

<400> SEQUENCE: 22
ttatcgataa gcttgatatc gaattc                                  26

<210> SEQ ID NO 23
<211> LENGTH: 21
<212> TYPE: DNA
<213> ORGANISM: Artificial Sequence
<220> FEATURE:
<223> OTHER INFORMATION: b2m forward primer

<400> SEQUENCE: 23
tgtgctcgcg ctactctctc t                                       21

<210> SEQ ID NO 24
<211> LENGTH: 21
<212> TYPE: DNA
<213> ORGANISM: Artificial Sequence
<220> FEATURE:
<223> OTHER INFORMATION: b2m reverse primer

<400> SEQUENCE: 24
cggatggatg aaacccagac a                                       21

-continued

<210> SEQ ID NO 25
<211> LENGTH: 21
<212> TYPE: DNA
<213> ORGANISM: Artificial Sequence
<220> FEATURE:
<223> OTHER INFORMATION: Ht2a forward primer

<400> SEQUENCE: 25
aactccagaa ctaaggcatt t                                              21

<210> SEQ ID NO 26
<211> LENGTH: 21
<212> TYPE: DNA
<213> ORGANISM: Artificial Sequence
<220> FEATURE:
<223> OTHER INFORMATION: Ht2a reverse primer

<400> SEQUENCE: 26
cttaaagacc ttcgaatcgt c                                              21

<210> SEQ ID NO 27
<211> LENGTH: 21
<212> TYPE: DNA
<213> ORGANISM: Artificial Sequence
<220> FEATURE:
<223> OTHER INFORMATION: Ht2b forward primer

<400> SEQUENCE: 27
cacgggctac agcattcatc a                                              21

<210> SEQ ID NO 28
<211> LENGTH: 21
<212> TYPE: DNA
<213> ORGANISM: Artificial Sequence
<220> FEATURE:
<223> OTHER INFORMATION: Ht2b reverse primer

<400> SEQUENCE: 28
ccaaaacgtt cctttgtcag c                                              21

<210> SEQ ID NO 29
<211> LENGTH: 21
<212> TYPE: DNA
<213> ORGANISM: Artificial Sequence
<220> FEATURE:
<223> OTHER INFORMATION: Ht2c forward primer

<400> SEQUENCE: 29
ccgagtccgt ttctcgtcta g                                              21

<210> SEQ ID NO 30
<211> LENGTH: 21
<212> TYPE: DNA
<213> ORGANISM: Artificial Sequence
<220> FEATURE:
<223> OTHER INFORMATION: Ht2c reverse primer

<400> SEQUENCE: 30
gatggcgtca gttggcctat g                                              21

<210> SEQ ID NO 31
<211> LENGTH: 20
<212> TYPE: DNA
<213> ORGANISM: Artificial Sequence
<220> FEATURE:

-continued

```
<223> OTHER INFORMATION: Her2/neu forward primer

<400> SEQUENCE: 31
cctctgacgt ccatcgtctc                                    20

<210> SEQ ID NO 32
<211> LENGTH: 20
<212> TYPE: DNA
<213> ORGANISM: Artificial Sequence
<220> FEATURE:
<223> OTHER INFORMATION: Her2/neu reverse primer

<400> SEQUENCE: 32
cggatcttct gctgccgtcg                                    20
```

RETARGETING OF VIRUSES OR VLPS

RELATED APPLICATIONS

This application is a § 371 national-stage application based on PCT/EP2018/052523 filed Feb. 1, 2018 which claims the benefit of priority to European Patent Office Application No. 17154380.4 filed Feb. 2, 2017, both of which is hereby incorporated by reference in their entirety.

SEQUENCE LISTING

The instant application contains a Sequence Listing which has been submitted electronically in ASCII format and is hereby incorporated by reference in its entirety. Said ASCII copy was submitted in the international application to which this application claims priority.

The present invention relates to a method of producing a polyomavirus or polyomavirus-derived virus-like particle (VLP) carrying on its surface at least one targeting molecule that binds to a cell of interest, the method comprising the step of contacting the polyomavirus or polyomavirus-derived VLP with (i) the targeting molecule, wherein the at least one targeting molecule is glycosylated with at least one glycosyl residue that is recognised by the polyomavirus or polyomavirus-derived VLP; or (ii) a first interaction molecule, wherein the first interaction molecule is glycosylated with at least one glycosyl residue that is recognised by the polyomavirus or polyomavirus-derived VLP; and the at least one targeting molecule, wherein the at least one targeting molecule is conjugated to a second interaction molecule capable of interacting with the first interaction molecule. The present invention further relates to a polyomavirus or polyomavirus-derived virus-like particle (VLP), wherein the virus or VLP carries on its surface at least one targeting molecule that binds to a cell of interest, as well as to a polyomavirus or polyomavirus-derived VLP obtained or obtainable by the method of the invention. Furthermore, the present invention relates to a composition comprising said polyomavirus or polyomavirus-derived VLP and to the use of the polyomavirus or polyomavirus-derived VLP of the invention or the composition of the invention for use as a medicament. The present invention further relates to a kit comprising the polyomavirus or polyomavirus-derived VLP or the composition of the invention.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Viral vector based gene therapy holds the promise to serve as cure for a vast number of genetic diseases. With respect to the progressing developments of diverse therapeutic tools, including the CRISPR/Cas9 genome editing system, gene replacement or RNA interference therapies, viral vectors are once more in the focus of genetic research [1-5]. However, there are limitations of viral vectors for clinical usage including high costs of vector generation, specific targeting of the desired cell type and thus avoiding harm to non-targeted cells, and efficient incorporation of the genetic material into the target-cell [6]. Most of these bottlenecks hold true also for non-viral delivery tools, in particular the rapidly expanding field of nanoparticles for drug and gene delivery [7].

The specific targeting of a desired cell type can only be achieved when the viral tropism matches susceptibility towards the cell type. The JC polyomavirus (JCV), for example, was described to infect target cells bearing the 5-$HT_2$ serotonin receptor in combination with a cell surface exposed α2,6-linked sialic acid on the lactoseries tetrasaccharide c (LSTc) glycan, which defines the natural tropism of JCV [8-11]. The tropism of JCV is defined by several flexible loops in the major capsid protein VP1, located on the outer surface of mature capsids. These loops were described to be responsible for LSTc binding on the target-cell's surface [10]. In a second step, the 5-$HT_2$ serotonin receptor is recruited, facilitating viral entry in a clathrin-dependent process.

The closely related BK polyomavirus (BKV) and the polyomavirus simian virus 40 (SV40) show comparable, yet distinct, features of target cell recognition and infection. BKV and SV40 use different α2,3- and α2,8-linked sialic acid containing gangliosides as initial cell-surface markers: e.g. BKV recognizes GD2, GD3, GD1b and GT1b, while SV40 recognizes GM1 [10, 12, 13]. Once the viruses detect their target cell and establish contact via its specific gangliosides or LSTc, cell entry takes place, whereas JCV, BKV and SV40 use different pathways. BKV and SV40 enter cells by a caveolae-mediated mechanism, whereas JCV requires clathrin-dependent endocytosis [14]. It was postulated that the combination of differences in ganglioside recognition is the basis for the different cell-entry mechanism of these viruses and further determines their tropism towards different cell-types.

Numerous studies have been performed to alter the natural viral tropism for gene therapy, with the aim to safely and specifically deliver genetic material into therapy-relevant cells. Usually these retargeting approaches are based on either incorporating target-proteins into the envelope of a virus or by fusing them directly onto the viral-capsid [6].

Utilizing the closely related VP1 of murine Polyomavirus (MuPyV), it was for example demonstrated that modification of one of these loops (HI-Loop) with an antibody-binding motif (z-protein) could serve as platform to alter the viral tropism [15]. Based on this approach, it was possible to fuse the humanized antibody herceptin onto the VLPs surface, thereby retargeting them towards human epidermal growth factor receptor 2 (HER2/neu) positive cells [16].

Retargeting approaches have also been described for other polyomaviruses. In case of the polyomavirus simian virus 40 (SV40), for example, one retargeting approach has been described that utilizes a chemical crosslinker $(SM[PEG])_2$. For that purpose, a cystein residue was introduced on the outer surface of the viral capsid and this residue was used to chemically crosslink a human epithelial growth factor onto the VLP. With these retargeted VLPs, the authors were successful in transducing A431 cells [17].

Another possible way to alter tropism has been described for VLPs derived from the non-polyomavirus HPV16 [18] and is based on the introduction of a biotinylation site in the HPV16 L1 capsid protein. However, the introduction of a biotinylation-sequence into the viral capsid represents a significant change of the viral capsid. Moreover biotinylation of the VLP requires incubation with another enzyme, biotin-ligase, which would have to be removed after incubation and, thus, requires the introduction of a further preparatory step.

One major drawback of these currently available methods of retargeting viral vectors to specific target cells is that they all require a direct modification of the virus or VLP, typically via the incorporation or attachment of antibodies or peptide ligands. In most cases, these modification are covalent modifications. The preparation of such retargeting viral vectors is often accompanied by various problems, such as the identification of suitable linkers as well as the requirement for complicated purification proceedings, which often involve several purification steps that limit their practicality and suitability for use in humans. Moreover, although many attempts for different polyomaviruses have been described [15, 19, 20], these direct modifications with rather large proteins remain associated with problems with respect to proper viral capsid assembly, transduction efficiency and stability.

In EP1270586 A2, an approach for the retargeting of VLPs based on the use of cationic polymers as anchoring molecules for target cell-specific ligands has been described. As suitable cationic polymers, amino acid-based polymers (e.g. poly-lysine) or poly-alkylen-imine (such as e.g. polyethylenimine) are described as interaction partners to bind JCV VP1 VLPs. The target cell-specific ligand is then bound to the cationic polymer. Importantly, the interaction of said cationic polymer with the VLP surface is neither a specific nor a controlled interaction, but solely relies on the different charge of the VLP and the cationic polymer.

Thus, despite the fact that a lot of effort is currently being invested into the development of suitable vectors systems for the targeted transfection of specific cells, these systems typically suffer from a complicated handling and cost- and time-consuming preparation processes, as well as potential problems with assembly, efficiency and stability or a lack of specificity. Accordingly, there is still a need to provide novel approaches for preparing viral vectors that can be targeted to specific cells in a simple and efficient manner and that are based on retargeting molecules whose influence on viral capsid assembly, transduction efficiency and stability is as small as possible. Such methods would represent valuable research and therapeutic tools and would offer tremendous value to the field.

This need is addressed by the provision of the embodiments characterised in the claims.

Accordingly, the present invention relates to a method of producing a polyomavirus or polyomavirus-derived virus-like particle (VLP) carrying on its surface at least one targeting molecule that binds to a cell of interest, the method comprising the step of contacting the polyomavirus or polyomavirus-derived VLP with (i) the at least one targeting molecule, wherein the at least one targeting molecule is glycosylated with at least one glycosyl residue that is recognised by the polyomavirus or polyomavirus-derived VLP; or (ii) a first interaction molecule, wherein the first interaction molecule is glycosylated with at least one glycosyl residue that is recognised by the polyomavirus or polyomavirus-derived VLP; and the at least one targeting molecule, wherein the at least one targeting molecule is conjugated to a second interaction molecule capable of interacting with the first interaction molecule.

Polyomaviruses are a family of viruses whose natural hosts are primarily mammals and birds. They are un-enveloped double-stranded DNA viruses with a circular genome that is packaged in an icosahedral viral capsid of about 40-50 nanometers in diameter. Said capsid is composed of 72 pentamers of the VP1 protein, and each molecule of VP1 is associated with one molecule of either VP2 or VP3. Currently, there are 76 recognized species in this family. Non-limiting examples of polyomaviruses include e.g. the following human polyomaviruses: BK polyomavirus, JC polyomavirus, Merkel cell polyomavirus, trichodysplasia spinulosa polyomavirus, human polyomavirus 9, human polyomavirus 12, New Jersey polyomavirus, KI polyomavirus, WU polyomavirus, human polyomavirus 6, human polyomavirus 7, MW polyomavirus and STL polyomavirus. Another prominent example of a polyomavirus is SV40, which refers to Simian vacuolating virus 40 or Simian virus 40, a polyomavirus that is found in both monkeys and humans.

Many polyomaviruses are typically asymptomatic in most human populations studied. However, some polyomaviruses are associated with human disease, particularly in immunocompromised individuals. For example, the BK virus is associated with nephropathy in renal transplant and non-renal solid organ transplant patients, the JC virus is associated with progressive multifocal leukoencephalopathy, and the Merkel cell virus with Merkel cell cancer.

Virus-like particles are well known in the art and have been described, e.g. in Tegerstedt et al. [21]. One major advantage of VLPs is that they are not associated with any risk of reassembly as is possible when live attenuated viruses are used as viral vectors. VLP production has the additional advantage that it can be started earlier than production of traditional vaccines once the genetic sequence of a particular virus strain of interest has become available.

Depending on the proteins employed, most VLPs can self-assemble upon expression of the respective viral structural proteins, for example, structural proteins of the envelope or in the capsid. For VLPs obtained from JCV, for example, it is well known in the art that they spontaneously form upon expression of the major capsid protein VP1 only. Suitable sequences of VP1 as well as the appropriate conditions for facilitating VLP formation are known in the art and have been described, e.g. in Chang et al. (1997) and Goldmann et al. (1999) [22, 23]. In those cases where capsid proteins are employed that do not have the inherent property to self-assemble into a VLP, additional auxiliary factors such as e.g. the viral proteins VP2, VP3 as well as nuclear cell extracts can be added to achieve assembly into VLPs under otherwise dissociating conditions, as it was described for SV 40 [24]. Preferably, the VLP is composed of proteins that have the inherent property to self-assemble under suitable conditions in vivo and/or in vitro, such that no additional auxiliary factors are required for the formation of the VLP.

In accordance with the present invention, the VLPs are derived from polyomavirus. The term “derived”, as used in this context, means that the VLPs are assembled of viral proteins that are polyomavirus proteins, such as the capsid protein VP1 of a polyomavirus, e.g. the capsid protein VP1 of the human polyoma JC virus.

The VLP can be composed of one type of protein or of several different types of proteins. Preferably, the VLP is composed of one type of protein, preferably of one type of capsid protein.

It will be appreciated that the polyomavirus-derived VLPs can be obtained from a virus but can also be recombinantly produced by methods well known in the art. Recombinant production can be carried out in a variety of cell culture systems including mammalian cell lines, insect cell lines, yeast, prokaryotic and plant cells.

So far, VLPs from different virus families have been produced, including polyomavirus viruses, parvoviridae (e.g. adeno-associated virus), retroviridae (e.g. HIV), and flaviviridae (e.g. Hepatitis C virus). Depending on the host/vector system chosen, the isolation of recombinant VLPs can take place directly from the host cells, but also from the cell culture supernatant. One advantage of preparing VLPs recombinantly is that they can be obtained with high purity and in large amounts. A commonly employed expression system for the recombinant synthesis of VP1 relies on insect cells, for example the insect cell line Sf 158, and the introduction of DNA encoding VP1 into said cells by using baculoviruses.

In accordance with the method of the present invention, a virus or VLP is produced that carries on its surface at least one targeting molecule.

The term "on its surface", as used herein, denotes that the targeting molecule is located such that it is exposed to the environment surrounding the virus or VLP, i.e. it is located on the outside of the virus or VLP particle.

The term "targeting molecule", in accordance with the present invention, refers to a molecule that is capable of interacting with a moiety of interest, such as e.g. a (surface) protein on a cell of interest. Due to this capability, the targeting molecule can direct the virus or VLP to said moiety of interest and the cell on which this moiety is present, i.e. it "targets" the virus or VLP to said cell. For example, if particular cancer cells, e.g. HER2/neu positive breast- and colorectal cancer cells, represent the cell of interest, then a surface marker of said cancer cells, such as HER2/neu, can be chosen as the moiety of interest. The targeting molecule, in accordance with the present invention, would be any molecule capable of interacting with said marker (e.g. HER2/neu), such as e.g. antibodies, ligands etc., as discussed in more detail herein below.

In accordance with the present invention, the term "at least one targeting molecule" means that more than one single targeting molecule can be present. It also means that more than one molecular type of targeting molecule (i.e. different types of targeting molecules) can be present. In other words, the term "carries on its surface at least one targeting molecule" explicitly encompasses that more than one molecule of the targeting molecule is present and it also explicitly encompasses that more than one molecular type of targeting molecule (i.e. one or more targeting molecule(s)) can be present in accordance with the present invention.

In accordance with the present invention, a targeting molecule is a molecule that binds to said cell of interest, i.e. the "target cell". Preferably, the targeting molecule is a molecule that specifically binds to said cell of interest. As used herein, the term "a molecule that specifically binds" (also referred to herein as "a molecule that specifically interacts") refers to a molecule that binds to the respective cell of interest but does not or essentially does not cross-react with a different type of cell. Such a specificity can for example be achieved by choosing a moiety of interest that is only present on the target cell but is absent on all other cells. Cross-reactivity of a panel of molecules under investigation may be tested, for example, by assessing binding of said panel of molecules under conventional conditions to the cell of interest, as well as to a number of more or less (structurally and/or functionally) closely related cells. Only those molecules that bind to the cell of interest but do not or do not essentially bind to any of the other cells are considered specific for the cell of interest. In those cases where more than one molecular type of targeting molecule is present on the surface of the virus or VLP, it is preferred that said different types of targeting molecules are all specific for the same cell of interest.

The term "a molecule that essentially does not cross-react", as used herein, refers to a molecule that binds to the cell of interest, i.e. the target cell, with at least 5-times higher affinity than to a different cell, more preferably at least 10-times higher affinity, such as e.g. at least 50-times higher affinity, more preferably at least 100-times higher affinity, such as e.g. at least 250-times higher affinity. Even more preferably, it binds with at least 500-times higher affinity to the cell of interest than to a different cell and most preferably with at least 1.000-times higher affinity.

The method of the present invention comprises in a first alternative (i.e. alternative (i)) the step of contacting the polyomavirus or polyomavirus-derived VLP with the at least one targeting molecule, wherein the at least one targeting molecule is glycosylated with at least one glycoprotein or glycolipid recognised by the polyomavirus or polyomavirus-derived VLP.

The term "comprising", as used herein, denotes that further components and/or steps can be included in addition to the recited components and/or steps. However, this term also encompasses that the claimed subject-matter consists of exactly the recited components and/or steps.

The terms "contacting" and "bringing into contact", as used herein, are not particularly limited and include all means of contacting viruses/VLPs with targeting molecules, such as e.g. adding the targeting molecules to the viruses/VLPs in e.g. a suspension. Also envisaged herein is that once the targeting molecules have been brought into contact with the virus/VLP, a purification step is included to remove unbound targeting molecules. A non-limiting example of how to carry out the removal of unbound targeting molecule is e.g. size exclusion chromatography.

In accordance with the present invention, the at least one targeting molecule is glycosylated. To this end, any targeting molecule can be directly glycosylated with the desired glycosyl residue, or it can be fused with at least one glycoprotein or glycolipid comprising the desired glycosyl residue. The "glycosyl residue" can be any glycosyl group that is stably connected via a glycosidic bond with either the targeting molecule or with the glycoprotein or glycolipid, as long as the glycosyl residue is chosen such that it is recognised by the polyomavirus or polyomavirus-derived VLP to which the at least one targeting molecule is to be bound. In this context, the term "recognised" means that the respective virus or VLP has a natural tropism to said glycosyl residue and, hence, recognises and binds said glycosyl residue. It will be appreciated that it is not required that said glycosyl residue is recognised by only this one virus/VLP; instead, a glycosyl residue may mediate tropism for a variety of viruses/VLPs. However, it is also envisaged that a glycosyl residue is chosen that is only recognised—i.e. specifically recognised—by one particular type of virus/VLP, such as e.g. only by JCV but not by other viruses, such as BK virus or SV40. In those cases where more than one type of targeting molecule is employed, it is particularly preferred that all targeting molecules are glycosylated with the same glycosyl residue. This can be carried out by the same or by different means of glycosylation, including direct and indirect glycosylation as described herein. More preferably, all different types of targeting molecules are glycosylated with the same glycosyl residue via the same glycosylation method.

The term "at least" as used herein, such as e.g. the term "at least one glycosyl residue" or "at least one" refers to the specifically recited number (i.e. "one") but also to more than the specifically recited number. For example, the term "at least one glycosyl residue" encompasses also at least two, at least three, at least four, at least five different glycosyl residues, and so on. Furthermore, this term also encompasses exactly one, exactly two, exactly three, exactly four, exactly five different glycosyl residues, and so on.

As discussed herein above, viruses are known to have a natural tropism towards certain cell types. JCV, for example, has been described to infect target cells bearing a member of the 5-HT$_2$ serotonin receptor family in combination with a cell surface exposed α2,6-linked sialic acid (SA) on the lactoseries tetrasaccharide c (LSTc) glycan, which defines the natural tropism of JCV [8-11]. Additionally VLPs derived from different strains of JCV have been described to interact not only with LSTc, but also with different glycolipids and glycoproteins with oligosaccharides containing α2,3-α2,8-α2,6-SA. VLPs derived from the genotype 3 strain (WT3), for example, have been shown to bind gangliosides with α2,3- and α2,8-SA asialo-GM1, GM1, GM2, GD1a, GD1b, GD2, GT1a and GT1b [25]. In addition, mad-1 strain VLPs have been shown to bind α2,3-α2,8- and α2,6-SA, including gangliosides GM3, GD2, GD3, GD1b, GT1 b and GQ1b [26].

Similar observations have been published for other polyomaviruses, such as BK virus or SV40. For example, the molecules GD2, GD3, GD1b and GT1b have been described to mediate the natural tropism of the BK virus towards target cells carrying said gangliosides on their surface. It is presently considered that cell types such as e.g. human fibroblasts, human epithelial cells and human embryonic kidney cells may thus be target cells for the BK virus [27]. Further, the molecule GM1 has been described to mediate the natural tropism of the SV40 virus towards cells carrying this molecule. It has thus been suggested that cell types such as human fetal and newborn tissues may be targets for the SV40 virus [27].

Accordingly, glycosylating the at least one targeting molecule with such (a) glycosyl residue(s) enables the binding of said targeting molecule(s) to the virus or VLP that has a natural tropism for said glycosyl residue(s). Because interactions between glycosyl residues and VP1 are normally formed as direct or indirect hydrogen bonds, including water mediated hydrogen bonds, or as van der Waals contacts with defined residues of VP1, it is particularly preferred that the glycosyl residue(s) enable(s) the binding of said targeting molecule(s) to the virus or VLP via direct or indirect hydrogen bonds or via van der Waals contacts. For example, by glycosylating the targeting molecules with LSTc, the interactions take place via the terminal NeuNAc and the α2,6-sialic acid of the neighbouring Gal of LSTc [10].

As a consequence, said targeting molecules can be bound by JCV without any further need for covalent modifications of the viral or VLP surface in order to attach the targeting molecule(s).

Means and methods of glycosylating a protein of interest, such as the targeting molecules of the present invention, with a glycosyl residue, are well known in the art. For example, by choosing an appropriate expression system, recombinantly produced targeting molecules can be obtained that carry the desired glycosylation pattern, either directly or via a fusion with a glycoprotein or glycolipid. Where necessary, the expression system can be modified, for example by genetic alterations of the host cells employed for recombinant production, such as e.g. *Pichia pastoris* or mammalian cells. Such methods have been described in detail e.g. in Ahmad et al. 2014 [28]. Alternatively, the relevant glycosyl residue can also be attached to the targeting molecule(s) via established cross-linking methods, such as e.g. by using chemical linkers including, without being limiting, NHS-maleimide, carboxyl-amine linkers such as e.g. EDC (1-ethyl-3-(3-dimethylaminopropyl)carbodiimide hydrochloride). Again, this attachment can be a direct attachment of the glycosyl residue to the targeting molecule (s), or via an (indirect) attachment of the respective glycosyl residue to the targeting molecule(s), e.g. via employing a glycoprotein or glycolipid encompassing the respective glycosyl residue. Also in those cases where the at least one targeting molecule is a carbohydrate, the glycosylation can be carried out by methods well known in the art. For example, the glycosyl residue can be added to the targeting molecule(s) by a condensation reaction between the sugar moieties. Further means and methods of (directly or indirectly) attaching a glycosyl residue to the at least one targeting molecule of interest are known in the art and have been described, e.g. in Komagome et al. [26].

In accordance with the present invention, it is preferred that the at least one glycosylated targeting molecule is obtained by expression in an appropriate host system. Such a recombinant expression of glycosylated targeting molecules does not require any additional modification steps and is, hence, less work-intensive.

The method of the present invention comprises in another alternative (i.e. alternative (ii)) the step of contacting two interaction molecules with each other, wherein the two interaction molecules are capable of interacting with each other. The first interaction molecule is glycosylated with at least one glycosyl residue that is recognised by the polyomavirus or polyomavirus-derived VLP. The second interaction molecule is conjugated to the at least one targeting molecule. Preferably, said conjugation is a covalent binding of the second interaction molecule to the at least one targeting molecule.

The definitions provided above with regard to the first alternative, in particular with regard to the contacting and the glycosylation with at least one glycosyl residue that is recognised by the polyomavirus or polyomavirus-derived VLP, apply mutatis mutandis to this second alternative.

In accordance with this alternative, the at least one targeting molecule is not directly glycosylated with the glycosyl residue. Instead, the targeting molecule is conjugated, preferably covalently bound, to one interaction molecule and the glycosylation with the respective glycosyl residue is present on another interaction molecule. Both interaction molecules are chosen such that they interact with each other. Upon interaction, the targeting molecule is indirectly connected to the glycosyl residue, and hence glycosylated.

Suitable interaction molecules are well known in the art. Non-limiting examples include the avidin-biotin systems, including e.g. avidin-biotin, streptavidin-biotin and NeutrAvidin-biotin, as well as systems comprising antibodies and their respective ligands, glutathione and glutathione S-transferase (GST), Maltose-binding protein, FITC and anti-FITC, irreversible protein attachment systems (IPAS) as well as tags, such as FLAG-, Myc-, HA-, 1D4-, polyArg-, calmodulin, chitin-binding-, cellulose-binding, S-protein-, Strep- and His-tag and their respective interacting partners [29]. Further non-limiting examples include click-chemistry approaches, as well as UV-, thermo- and pH-dependent crosslinking [30]. Additional non-limiting approaches include split-protein approaches to fuse targeting- and LSTc-glycosylated proteins, or bi-functional antibodies that enable stable interactions of e.g. VP1-binding carbohydrates and target-cell structures [31-36].

In both alternatives, the method of the present invention encompasses that (directly or indirectly) glycosylated targeting molecules are contacted with a polyomavirus or polyomavirus-derived VLP. This contacting results in the binding of the targeting molecule(s) to the virus or VLP, via the glycosyl residue. The virus or VLP is thus no longer targeted to the respective glycosyl residue on a cell surface, but instead becomes re-targeted to the cell of interest to which the at least one targeting molecule is capable of binding.

Thus, the present invention provides a novel approach for the targeting of viruses and virus-like particles to cells of interest. This approach relies on the viruses/VLPs natural tropism to certain glycosyl residues, which normally serve as surface markers on target cells. These glycosyl residues are now employed to mediate the binding of different targeting molecules, which can be targeted to any cell of interest, entirely independently of the natural target cells of said virus or VLP. Even more, binding of the targeting molecules can additionally be employed to "mask" the binding sites on the virus or VLP for their natural target cells.

Previous approaches, such as e.g. the modification of one of the flexible loops in the major capsid protein VP1 with an antibody-binding motif as described in [15] suffered from the drawback that in a first step, a modification of the virus/VLP is required. Also the covalent coupling of targeting molecules to the surface of a virus or VLP requires in a first step this modification of the virus or VLP. These initial steps mean that additional, cumbersome procedural steps have to be carried out, that are not only time- but also cost-consuming. As the processes for the preparation of viruses and VLPs for therapeutic approaches are already rather demanding processes that require highly refined process conditions and analytical monitoring, it would be preferable to avoid any additional method steps unless absolutely necessary. Moreover, including such modification steps also means that additional laborious purification steps are required, further adding to the complexity of the preparation process. These technical limitations have severely limited the development of novel retargeting systems in the past.

The present invention, on the other hand, provides a method of producing viruses or VLPs that can be targeted to a plethora of different cells of interest, without the initial cumbersome modification and purification steps of the viruses or VLPs required by prior art methods. The viruses and VLPs thus obtained find applicability in many different fields, e.g. as carriers for transducing target cells with nucleic acid molecules of interest, for example for gene therapy, or for the targeted delivery of substances to target cells, such as e.g. cytotoxic compounds to cancer cells.

In a preferred embodiment of the method of the invention, the polyomavirus is the human polyoma JC virus or the VLP is derived from the human polyoma JC virus.

The JC virus (also referred to as John Cunningham virus) is abbreviated JCV and is a human polyomavirus that is genetically similar to BK virus and SV40. It causes progressive multifocal leukoencephalopathy (PML) and other diseases, but only in cases of immunodeficiency, as in AIDS or during treatment with immunosuppressive drugs (e.g. in organ transplant patients). 14 subtypes or genotypes are recognized, each associated with a specific geographical region. In an alternative numbering scheme, the genotypes are numbered 1 to 8 with additional lettering. The natural host spectrum of JCV comprises cells of neural and related tissues, such as, for example, oligodendrocytes, astrocytes, and glial cells.

All definitions and preferred embodiments provided herein above with regard to the polyomavirus or polyomavirus-derived VLPs apply mutatis mutandis to this preferred embodiment.

In a further preferred embodiment of the method of the invention, the VLP comprises the capsid protein VP1 of the human polyoma JC virus.

In as far as the VLP comprises (instead of consisting of) the capsid protein VP1 of the human polyoma JC virus, it is particularly preferred that the VLP is free from other components of the authentic virus, such as, for example, authentic viral nucleic acids. Even more preferably, the VLP "consists" of the capsid protein VP1 of the human polyoma JC virus, i.e. there are no other viral capsid proteins present. It will be appreciated that even in the case that the VLP "consists" of the capsid protein VP1, this VLP nonetheless contains the targeting molecule(s) attached to the surface of the VLP, in accordance with the present invention. Furthermore, it is optionally envisaged that a VLP that "consists" of the capsid protein VP1 may optionally contain additional cargo molecules, or additional targeting moieties (provided that said additional targeting moieties are not viral capsid proteins), as defined in more detail herein below. In other words, the definition that the VLP "consists" of the capsid protein VP1 of the human polyoma JC virus means that the molecules that build the VLP, i.e. the carrier (without referring to its cargo or attached molecules) does only consist of VP1 proteins.

The term "capsid protein VP1", as used herein, relates to the capsid protein VP1 of the wild type strain of the human polyoma JC virus, as well as to modified forms of this capsid protein, i.e. proteins that differ from the wild type-capsid protein by mutations, such as, for example, substitutions, insertions, and/or deletions. The capsid protein VP1 of the wild type strain of the human polyoma JC virus is known in the art and is represented by Gene ID: 1489518 (as updated on the NCBI database on 20 Aug. 2016) or by UniProt ID P03089 (as available on Sep. 14, 2016). The coding sequence of VP1 is also shown in SEQ ID NO:1, while its amino acid sequence is shown in SEQ ID NO:2.

In a more preferred embodiment, the VLP is composed of recombinantly produced capsid protein. For producing recombinant VP1, preferably a nucleic acid molecule is used that comprises, and preferably consists of, (i) the nucleic acid molecule of SEQ ID NO:1,
(ii) a nucleic acid molecule of the sequence of SEQ ID NO:1, wherein each thymine is replaced by uracil;
(iii) a nucleic acid molecule that hybridizes under stringent conditions to the complementary strand of a nucleic acid molecule of (i) or (ii)
(iv) a nucleic acid molecule having at least 85% sequence identity to the nucleic acid molecule of (i); or
(v) a nucleic acid molecule that is degenerate with respect to the nucleic acid molecule of (i) to (iii).

Means and methods of producing a recombinant protein from a nucleic acid molecule are well known in the art. For example, the nucleic acid molecule or a (recombinant) vector containing this nucleic acid molecule can be introduced into a suitable host cell, the host cell is then cultured under conditions enabling the expression of the respective nucleic acid molecule, and the protein is isolated from the cell or the cellular supernatant.

"Stringent conditions", as used herein, refers to hybridization conditions under which the nucleic acid molecules that are capable of hybridizing to the nucleic acid molecule of interest over the entire length of the nucleic acid molecule of interest, do not cross hybridize with unrelated nucleic acid molecules. Stringent conditions are sequence-dependent and will be different in different circumstances. Appropriate stringent hybridization conditions for each nucleic acid sequence may be established by a person skilled in the art on well-known parameters such as temperature, composition of the nucleic acid molecules, salt conditions etc.; see, for example, Sambrook et al., "Molecular Cloning, A Laboratory Manual"; CSH Press, Cold Spring Harbor, 1989 or Higgins and Hames (eds.), loc. cit., see in particular the chapter "Hybridization Strategy" by Britten & Davidson, 3 to 15.

In accordance with option (iv) cited above, it is particularly preferred that for the recombinant production of a VP1-polypeptide a nucleic acid molecule is used that is identical to the nucleic acid sequence of SEQ ID NO:1 to at least 85%, preferably to at least 90%, particularly preferred to at least 95%, and most preferred to at least 98%, wherein the identity is determined over the whole length of SEQ ID NO: 1.

The amino acid sequence encoded by the nucleic acid molecule of SEQ ID NO:1 is shown in SEQ ID NO:2. As detailed above, the VP1 protein can also be a modified VP1 protein. P The preferred degrees of sequence identity recited in the preceding paragraph for the nucleic acid molecule apply mutatis mutandis to these modified forms of the capsid protein VP1, i.e. it is preferred that the modified VP1 protein is at least 85%, preferably at least 90%, more preferably at least 95% and most preferably at least 98% identical to the VP1 protein consisting of the amino acid sequences of SEQ ID NO:2, wherein the identity is determined over the whole length of SEQ ID NO: 2.

Preferably, the modified VP1 protein is a protein wherein the amino acid sequence is modified in the N-terminal region, for example within the region of the N-terminal 25 amino acids. A particularly preferred modification is the introduction of a heterologous nuclear localization signal. Preferred nuclear localization signals contain the amino acid sequence CPGAAP (SEQ ID NO:5) or the amino acid sequence $X_1X_2P$, wherein $X_1$ and $X_2$ mean arbitrary amino acids, preferably K, respectively, and which are based, for example, on the amino acid sequences of nuclear localization signals of SV40 or BKV. The nucleic acid sequence encoding for such a preferred modified VP1 protein (VP1-Mut2) is shown in SEQ ID NO:3. The corresponding amino acid sequence is shown in SEQ ID NO: 4.

In another preferred embodiment of the method of the invention, the glycosyl residue contains an α2,3-α2,8- or α2,6-SA and, preferably, is selected from lactoseries tetrasaccharide c (LSTc), GM1, asialo-GM1, GM2, GD1a, GD1b, GD2, GT1a, GT1b, GM3, GD3, and GQ1b.

As used herein, the term "lactoseries tetrasaccharide c", also abbreviated as LSTc herein, refers to sialyllacto-N-neotetraose c with the UIPAC name (2R,4S,5R,6R)-5-acetamido-2-[[(3R,4S,5R,6S)-6-[(2R,3S,4R,5R,6S)-5-acetamido-6-[(2R,3S,4S,5R,6S)-3,5-dihydroxy-2-(hydroxymethyl)-6-[(2R,3R,4R,5R)-1,2,4,5-tetrahydroxy-6-oxohexan-3-yl]oxyoxan-4-yl]oxy-4-hydroxy-2-(hydroxymethyl)oxan-3-yl]oxy-3,4,5-trihydroxyoxan-2-yl]methoxy]-4-hydroxy-6-[(1R,2R)-1,2,3-trihydroxypropyl]oxane-2-carboxylic acid and has the PubChem CID 53477861 (as available on Oct. 18, 2016).

In accordance with the present invention, the term "GM1" relates to the ganglioside monosialotetrahexosylganglioside with the UIPAC name (2S,4S,5R,6R)-5-acetamido-2-[(2S,3R,4R,5S,6R)-5-[(2S,3R,4R,5R,6R)-3-acetamido-5-hydroxy-6-(hydroxymethyl)-4-[(2R,3R,4S,5R,6R)-3,4,5-trihydroxy-6-(hydroxymethyl)oxan-2-yl]oxyoxan-2-yl]oxy-2-[(2R,3S,4R,5R,6R)-4,5-dihydroxy-6-[(E,2R,3S)-3-hydroxy-2-(icosanoylamino)icos-4-enoxy]-2-(hydroxymethyl)oxan-3-yl]oxy-3-hydroxy-6-(hydroxymethyl)oxan-4-yl]oxy-4-hydroxy-6-[(1R,2R)-1,2,3-trihydroxypropyl]oxane-2-carboxylic acid and has the PubChem CID 9963963 (as available on Oct. 14, 2016).

The term "asialo-GM1", in accordance with the present invention, relates to the ganglioside ganglio-N-tetraosylceramide with the UIPAC name N-[(E)-1-[(3R,4R,5S,6R)-5-[(2S,3R,4R,5R,6R)-5-[(2S,3R,4R,5R,6R)-3-acetamido-5-hydroxy-6-(hydroxymethyl)-4-[(2R,3R,4S,5R,6R)-3,4,5-trihydroxy-6-(hydroxymethyl)oxan-2-yl]oxyoxan-2-yl]oxy-3, 4-dihydroxy-6-(hydroxymethyl)oxan-2-yl]oxy-3,4-dihydroxy-6-(hydroxymethyl)oxan-2-yl]oxy-3-hydroxyoctadec-4-en-2-yl]octadecanamide and has the PubChem CID 6450363 (as available on Oct. 18, 2016).

The term "GM2", in accordance with the present invention, relates to the ganglioside GM2 with the IUPAC name 5-acetamido-2-[[5-[3-acetamido-4,5-dihydroxy-6-(hydroxymethyl)oxan-2-yl]oxy-2-[4,5-dihydroxy-2-(hydroxymethyl)-6-[3-hydroxy-2-(octadecanoylamino)octadec-4-enoxy]oxan-3-yl]oxy-3-hydroxy-6-(hydroxymethyl)oxan-4-yl]oxymethyl]-4-hydroxy-6-(1,2,3-trihydroxypropyl)oxane-2-carboxylic acid and has the PubChem CID 92039511 (as available on Oct. 18, 2016).

The term "GM3", in accordance with the present invention, relates to the ganglioside GM3 with the IUPAC name (2S,4S,5R)-5-acetamido-2-[(2S,3R,4S,5S,6R)-2-[(2R,3S,4R,5R,6R)-6-[(E,2S,3R)-2-[[(Z)-docos-13-enoyl]amino]-3-hydroxyoctadec-4-enoxy]-4, 5-dihydroxy-2-(hydroxymethyl)oxan-3-yl]oxy-3,5-dihydroxy-6-(hydroxymethyl)oxan-4-yl]oxy-4-hydroxy-6-[(1R,2R)-1,2,3-trihydroxypropyl]oxane-2-carboxylic acid and has the PubChem CID 53481206 (as available on Oct. 18, 2016).

In accordance with the present invention, the term "GD1a" relates to ganglioside GD1a with the IUPAC name (2R,4S,5R,6R)-2-[[(2R,3S,4S,5R,6S)-4-[(2S,4S,5R,6R)-5-acetamido-2-carboxy-4-hydroxy-6-[(1R,2R)-1,2,3-trihydroxypropyl]oxan-2-yl]oxy-6-[(2R,3R,4R,5R,6S)-5-acetamido-6-[(2R,3R,4R,5R,6S)-6-[(2R,3S,4R,5R,6R)-4,5-dihydroxy-2-(hydroxymethyl)-6-[(E,2S,3R)-3-hydroxy-2-(octadecanoylamino)octadec-4-enoxy]oxan-3-yl]oxy-4,5-dihydroxy-2-(hydroxymethyl)oxan-3-yl]oxy-4-hydroxy-2-(hydroxymethyl)oxan-3-yl]oxy-3,5-dihydroxyoxan-2-yl]methoxy]-4-hydroxy-5-[(2-hydroxyacetyl)amino]-6-[(1R,2R)-1,2,3-trihydroxypropyl]oxane-2-carboxylic acid; azane and has the PubChem CID 102601600 (as available on Oct. 18, 2016).

As used herein, the term "GD1b" refers to GD1b-ganglioside with the IUPAC name (2S,4S,5R,6R)-5-acetamido-2-[(2S,3R,4R,5S,6R)-5-[(2S,3R,4R,5R,6R)-3-acetamido-5-hydroxy-6-(hydroxymethyl)-4-[(2R,3R,4S,5R,6R)-3,4,5-trihydroxy-6-(hydroxymethyl)oxan-2-yl]oxyoxan-2-yl]oxy-2-[(2R,3S,4R,5R,6R)-4,5-dihydroxy-2-(hydroxymethyl)-6-[(E)-3-hydroxy-2-(octadecanoylamino)octadec-4-enoxy]oxan-3-yl]oxy-3-hydroxy-6-(hydroxymethyl)oxan-4-yl]oxy-6-[(1S,2R)-2-[(2S,4S,5R,6R)-2-carboxy-4-hydroxy-5-[(2-hydroxyacetyl)amino]-6-[(1R,2R)-1,2,3-trihydroxypropyl]oxan-2-yl]oxy-1,3-dihydroxypropyl]-4-hydroxyoxane-2-carboxylic acid and has the PubChem CID 92132037 (as available on Oct. 18, 2016).

The term "GD2", in accordance with the present invention, relates to GD2-Ganglioside with the IUPAC name (2R,4R,5S,6S)-2-[3-[(2S,3S,4R,6S)-6-[(2S,3R,4R,5S,6R)-5-[(2S,3R,4R,5R,6R)-3-acetamido-4,5-dihydroxy-6-(hydroxymethyl)oxan-2-yl]oxy-2-[(2R,3S, 4R,5R,6R)-4,5-dihydroxy-2-(hydroxymethyl)-6-[(E)-3-hydroxy-2-(octadecanoylamino) octadec-4-enoxy]oxan-3-yl]oxy-3-hydroxy-6-(hydroxymethyl)oxan-4-yl]oxy-3-amino-6-carboxy-4-hydroxyoxan-2-yl]-2,3-dihydroxypropoxy]-5- amino-4-hydroxy-6-(1,2,3-trihydroxypropyl)oxane-2-carboxylic acid and has the PubChem CID 6450346 (as available on Oct. 18, 2016).

The term "GD3", in accordance with the present invention, relates to the ganglioside GD3 with the IUPAC name 5-acetamido-6-[(1S,2R)-2-[5-acetamido-2-carboxylato-4-hydroxy-6-[(1R,2R)-1,2,3-trihydroxypropyl]oxan-2-yl]oxy-1,3-dihydroxypropyl]-2-[2-[4,5-dihydroxy-2-(hydroxymethyl)-6-[(E,2S,3R)-3-hydroxy-2-(tricosanoylamino)octadec-4-enoxy]oxan-3-yl]oxy-3,5-dihydroxy-6-(hydroxymethyl)oxan-4-yl]oxy-4-hydroxyoxane-2-carboxylate and has the PubChem CID 16760459 (as available on Oct. 18, 2016).

In accordance with the present invention, the term "GT1a" relates to the polysialoganglioside with the IUPAC name (2R,4S,5R,6R)-2-[(2S,3S,4R,5R,6S)-2-[(2R,3S,4S,5S,6S)-3-acetamido-2-[(2S,3R,4S,5S,6R)-4-[(2R,4S,5R,6R)-5-amino-2-carboxy-4-hydroxy-6-(1,2,3-trihydroxypropyl)oxan-2-yl]oxy-6-[(2R,3S,4R,5R,6R)-4,5-dihydroxy-2-(hydroxymethyl)-6-[(E)-3-hydroxy-1-(octadecanoylamino)octadec-4-en-2-yl]oxyoxan-3-yl]oxy-5-hydroxy-2-(hydroxymethyl)oxan-3-yl]oxy-5-hydroxy-6-(hydroxymethyl)oxan-4-yl]oxy-3,5-dihydroxy-6-(hydroxymethyl)oxan-4-yl]oxy-5-amino-6-[2-[(2R,4S,5R,6R)-5-amino-2-carboxy-4-hydroxy-6-(1,2,3-trihydroxypropyl)oxan-2-yl]oxy-1,2-dihydroxyethyl]-4-hydroxyoxane-2-carboxylic acid and has the PubChem CID 6450319 (as available on Oct. 18, 2016).

In accordance with the present invention, the term "GT1b" relates to GT1b ganglioside (C36) with the IUPAC name (2S,4S,5R,6R)-5-acetamido-2-[(2R,3R,4S,5S,6R)-2-[(2S,3R,4R,5R,6R)-3-acetamido-2-[(2R,3S,4R,5R,6S)-4-[(2S,4S,5R,6R)-5-acetamido-6-[(1S,2R)-2-[(2S,4S,5R,6R)-5-acetamido-2-carboxy-4-hydroxy-6-[(1R,2R)-1,2,3-trihydroxypropyl]oxan-2-yl]oxy-1,3-dihydroxypropyl]-2-carboxy-4-hydroxyoxan-2-yl]oxy-6-[(2R,3S,4R,5R,6R)-4,5-dihydroxy-2-(hydroxymethyl)-6-[(E,2S,3R)-3-hydroxy-2-(octadecanoylamino)octadec-4-enoxy]oxan-3-yl]oxy-5-hydroxy-2-(hydroxymethyl)oxan-3-yl]oxy-5-hydroxy-6-(hydroxymethyl)oxan-4-yl]oxy-3,5-dihydroxy-6-(hydroxymethyl)oxan-4-yl]oxy-4-hydroxy-6-[(1R,2R)-1,2,3-trihydroxypropyl]oxane-2-carboxylic acid and has the PubChem CID 14181654 (as available on Oct. 18, 2016).

In a particularly preferred embodiment of the method of the invention, the glycosyl residue is lactoseries tetrasaccharide c (LSTc).

In a further preferred embodiment of the method of the invention, the at least one targeting molecule is selected from a protein, a peptide or a carbohydrate. It will be appreciated that in those cases where more than one targeting molecule is employed, said targeting molecules can be independently selected from proteins, peptides and carbohydrates, i.e. they can be different from each other.

The term "peptide", as used herein, describes a group of molecules consisting of up to 30 amino acids, whereas "proteins" consist of more than 30 amino acids. Peptides and proteins may further form dimers, trimers and higher oligomers, i.e. consisting of more than one molecule which may be identical or non-identical. The corresponding higher order structures are, consequently, termed homo- or heterodimers, homo- or heterotrimers etc. The terms "peptide" and "protein" (wherein "protein" is interchangeably used with "polypeptide") also refer to naturally modified peptides/proteins wherein the modification is effected e.g. by glycosylation, acetylation, phosphorylation and the like. Such modifications are well-known in the art. Furthermore, peptidomimetics of such peptides and proteins where amino acid(s) and/or peptide bond(s) have been replaced by functional analogues are also encompassed herein. Such functional analogues include all known amino acids other than the 20 gene-encoded amino acids, such as selenocysteine. Specific, preferred, examples of suitable proteins or peptides are detailed herein below.

The term "carbohydrate", as used herein, refers to any types of carbohydrates. Both naturally occurring carbohydrates as well as chemically modified carbohydrates are encompassed by this term. Carbohydrates are typically divided into four chemical groups: monosaccharides, disaccharides, oligosaccharides, and polysaccharides. Preferably, the carbohydrates in accordance with the present invention are any disaccharides or oligosaccharides as well as alcohols thereof. Preferred components for disaccharides and oligosaccharides include, without being limiting, glucose, mannose, fucose, galactose, N-acetylgalactosamine, and pullulan.

Several cell-surface molecules are capable of binding to carbohydrates, in particular to di- or oligosaccharides. For example, lectins are capable of recognizing different carbohydrate moieties, leading to the uptake of the respective molecules. Furthermore, liver cells such as liver parenchymal cells express the asialoglycoprotein receptor (ASGP-R), which can recognise a wide variety of desialylated glycoproteins and neoglycoproteins that contain terminal β-D-galactose or N-acetylgalactosamine residues, but also other saccharide residues such as mannose, lactose or fructose and acids derived therefrom, like e.g. lactobionic acid [37-39].

By choosing an appropriate carbohydrate as a targeting molecule, target cells carrying the respective receptors such as e.g. human hepatocellular carcinoma cells can be targeted.

In a more preferred embodiment of the method of the invention, the at least one targeting molecule is a protein selected from an antibody, transferrin, epidermal growth factor (EGF) family members, a cytokine, a partial viral glycoprotein, CD9, var2csa, insulin or a ligand for GABA. Again, it will be appreciated that in those cases where more than one targeting molecule is employed, said targeting molecules can be independently selected from the recited proteins, i.e. they can be different from each other.

An antibody in accordance with the present invention can be, for example, a polyclonal or monoclonal antibody. The term "antibody", as used herein, also includes embodiments such as chimeric (human constant domain, non-human variable domain), single chain and humanized (human antibody with the exception of non-human CDRs) antibodies, as well as antibody fragments, like, inter alia, Fab, Fab', Fd, F(ab')$_2$, Fv or scFv fragments or nanobodies, i.e. single monomeric variable antibody domains; see, for example, Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. Techniques for the production of antibodies are well known in the art and have been described, e.g. in Harlow and Lane (1988) and (1999), loc. cit.

Preferably, the antibody is an antibody capable of binding to cancer cell markers such as e.g. Her2/neu, carcinoembryogenic antigen, CD33, CD34, or chondroitin sulfate A.

The term "transferrin", as used herein, relates to a glycoprotein, which binds iron as a blood plasma protein and thus is involved in cellular iron ion delivery. Two transferrin receptors have been described in humans, transferrin receptor 1 (TfR1) (UniProtKB-P02786) and transferrin receptor 2 (TfR2) (UniProtKB-Q9UP52). Both receptors are transmembrane glycoproteins, with TfR1 being an ubiquitously expressed receptor and TfR2 being restricted to hepatocytes and erythrocytes [40].

The term "epidermal growth factor (EGF) family members", as used herein, relates to the family of human epidermal growth factor proteins, which interact with epidermal growth factor receptors. Non-limiting examples of family members include e.g. EGF (UniProtKB P01133), transforming-growth factor α (UniProtKB-P01135) or heparin-binding EGF-like growth factor (UniProtKB-Q99075).

The term "cytokine", as used herein, relates to peptides which control cell proliferation and differentiation. Non-limiting examples of cytokines include interleukins (e.g. IL-2, IL-6, IL-10), interferons (e.g. IFN-α, IFN-β and IFN-γ), colony-stimulating factors (CSFs) and tumor necrosis-factors (TNFs).

In accordance with the present invention, the term "partial viral glycoprotein" refers to the epitope-recognition sequence of viral glycoproteins, without their respective membrane- or capsid-anchor. Non-limiting examples of partial viral glycoproteins include EnvA, VSV-G or the HIV-1 GP160.

The term "EnvA", as used herein, relates to the envelope glycoprotein gp95 of avian leukosis virus and is represented by UniProtKB-P03397 (as available on Oct. 14, 2016).

The term "VSV-G", as used herein, relates to the spike glycoprotein g of the vesicular stomatitis virus and is represented by UniProtKB-P04882 (as available on Oct. 14, 2016).

The term "HIV-1 GP160", as used herein, relates to the envelope glycoprotein gp160 of the human immunodeficiency virus type 1and is represented by UniProtKB-P03375 (as available on Oct. 14, 2016).

The term "CD9", as used herein, relates to the tetraspanin-family member CD9. CD9 has the accession number UniProtKB-P21926 (as available on Oct. 14, 2016).

In accordance with the present invention, the term "var2csa" refers to a *Plasmodium falciparum* var2 gene family member PfEMP1 (UniProtKB-096108, as available on Oct. 14, 2016), whose gene-product is able to bind chondroitin-sulphate A.

The term "insulin", as used herein, relates to human insulin and is represented by UniProtKB-P01308 (as available on Oct. 14, 2016).

As used herein, the term "ligand for GABA" relates to any molecule that can serve as a ligand for one (or more) of the GABA-receptor family members i.e. $GABA_A$-ρ or $GABA_B$. Non-limiting examples of suitable ligands for GABA include imidazole-4-acetic acid, muscimol, isoguvacine and THIP [41].

By employing the above cited targeting molecules, the viruses or VLPs can be re-targeted to disease-relevant target cells. For example, the use of antibodies is suitable to target the viruses or VLPs to any cell that expresses the antigen for said antibody, such as e.g. to Her2/neu-expressing cancer cells when using an anti-Her2/neu antibody. Similarly, the use of EGF family members, such as e.g. epidermal growth factor (EGF) itself, as targeting molecule enables VLPs to target EGF-receptor-expressing cancer cells. Transferrin enables VLP-targeting to cells that expressing a transferrin-receptor and therefore allows for a targeting of an extremely broad variety of target cells and tissues. Utilization of intact or partial insulin enables VLP-targeting to beta-cells and other cell types exposing insulin receptors. Cytokines are well suited to interact with their respective receptors and when used as targeting molecule(s) they can mediate uptake into a variety of cells types of the myeloid or lymphoid lineages. GABA ligands can mediate specific targeting of VLPs to cells within the peripheral or central nervous system. Finally, by employing partial viral glycoproteins the virus or VLP can be retargeted to the respective receptors that the corresponding viruses utilize for host infection and, thus, may enable the utilization of such re-targeted VLPs to treat or prevent the viral infection. In summary, the thus re-targeted viruses or VLPs offer a broad range of uses, including therapeutic and research application. For example, and as discussed in more detail below, numerous diseases can be investigated by researchers and/or treated by clinicians by employing such viruses or VLPs carrying e.g. the relevant cargo molecules for gene therapy approaches, for RNA interference approaches, as well as for DNA-based tumour vaccination approaches.

In another more preferred embodiment of the method of the invention, the at least one targeting molecule is a peptide selected from substance-P, an opioid or cell-penetrating peptides. Again, it will be appreciated that in those cases where more than one targeting molecule is employed, said targeting molecules can be independently selected from these peptides, i.e. they can be different from each other.

The term "substance-P", as used herein, relates to the neurokinine oligopeptide-family member with the sequence RPKPQQFFGLM (SEQ ID NO:6). Substance P is in particular suitable to aid the transfer of cargos into cells that expose the neurokinine type 1 receptor (NK1R), including neuronal tissue and certain types of cancer including colorectal carcinoma [42, 43]. Substance P utilization as targeting molecule is therefore envisaged to enable the treatment of disorders that relate to cells of the peripheral or central nervous system and to the treatment of cancer types that expose NK1R.

The term "opioid", as used herein, relates to any substance that acts on an opioid receptor, such as e.g. the delta opioid receptors (DOR), the kappa opioid receptors (KOR), the mu opioid receptors (MOR), the nociceptin receptors (NOR) or the zetta opioid receptors (ZOR). Opioids include compounds derived from opium, including e.g. morphine, as well as semi-synthetic and synthetic compounds, e.g. hydrocodone, oxycodone and fentanyl, antagonistic compounds, e.g. naloxone, or endogenous peptides, such as endorphins. Opioid receptors are widely distributed in the brain, but are also found in the spinal cord and the digestive tract.

Accordingly, by choosing an appropriate opioid as the targeting molecule, target cells carrying opioid receptor such as e.g. peripheral sensory neurons (target cells for DOR, MOR, KOR), basal ganglia and neocortical regions of the brain (target cells for DOR) [44], spinal cord (target cells for KOR, MOR, NOR) or heart, skeletal muscle and liver cells (target cells for ZOR) [45, 46] can be targeted.

The term "cell-penetrating peptides" (CPP), as used herein, relates to short cationic peptides like antennapedia, TAT, transportan and polyarginine, which have been described in the art as tools for peptide-delivery [47]. CPPs can mediate translocation of attached cargos across the cell membrane and are, therefore, particularly suited to act as targeting and/or entry molecule for VLPs and viruses.

In a further preferred embodiment of the method of the invention, the first and second interaction molecules are avidin and biotin, streptavidin and biotin or NeutrAvidin and biotin.

The avidin-streptavidin system of interacting molecules, including the variations streptavidin-biotin and NeutrAvidin-biotin, is well known in the art and has been described in e.g. Dundas et al. 2013. Streptavidin binds its interaction partner biotin with a high selectivity and a $k_D$ in the nM range. Moreover Streptavidin is stable against high temperatures and over a broad pH. Latest improvements gave rise to single-domain streptavidin-proteins, allowing a more controlled approach in terms of binding-stoichiometry [48].

In accordance with this preferred embodiment, the choices of the first and second interaction molecules are not limited to the recited order. In other words, if the first and second interaction molecules are avidin and biotin, it is envisaged that either (i) avidin is the first interaction molecule and biotin is the second interaction molecule; or (ii) biotin is the first interaction molecule and avidin is the second interaction molecule. The same applies mutatis mutandis to the other recited combinations of interaction molecules, i.e. streptavidin and biotin as well as NeutrAvidin and biotin.

In another preferred embodiment of the method of the invention, the virus or VLP further comprises one or more cargo molecules within the virus or VLP.

The term "one or more", as used herein, encompasses exactly one as well as any number above one, such as e.g. two, three, four, five, six, seven, eight, nine, ten and so on. Preferably, the virus or VLP comprises at most 400 cargo molecules, in the case of siRNA preferably at most 300 molecules.

The term "cargo molecules", in accordance with the present invention, relates to molecules to be transported by the virus or VLP of the invention. Non-limiting examples of cargo molecules include nucleic acid molecules, in particular modulating nucleic acid molecules, toxins, proteins, such as e.g. enzymes, peptides as well as other small molecules, such as e.g. propidium-iodid. Preferably, said cargo molecules are pharmaceutical compound or drugs for therapeutic or research purposes.

Means and methods to include cargo molecules in viruses or VLPs are well known in the art and have been described, e.g. in Teunissen et al. 2013. [49]. More specifically, the use of VLPs as a drug delivery system for nucleic acid molecules has been described in detail in e.g. WO2009/036933. Delivery of proteins and low molecular substances via VLPs has been described e.g in Abbing et al. 2004 [50]. As described in this reference, it is advantageous to couple the cargo molecule to the inner surface of the VLP, for example by ensuring an interaction of the cargo molecule with VP2. These approaches are well known to the person skilled in the art, e.g. from Abbing et al. 2004 [50].

In a preferred embodiment, the cargo molecules are nucleic acid molecules. Non-limiting examples of suitable nucleic acid molecules include nucleic acid molecules for vaccination purposes as well as modulating nucleic acid molecules, such RNA interference inducing molecules.

Preferably, the RNA interference inducing molecule is an RNA, such as e.g. a dsRNA, (including e.g. siRNA), miRNA, shRNA or a precursor thereof, and/or an RNA analogue. In an alternative, it is preferred that the RNA interference inducing molecule is a DNA and/or a DNA analogue, which encodes a dsRNA (including e.g. an siRNA), miRNA, shRNA or a precursor thereof. It will be appreciated that such a DNA molecule may comprise further regulatory elements that ensure the expression of the RNA interference inducing molecule in the target cell.

Such nucleic acid molecules suitable as cargo molecules are well known in the art and have been described, e.g. in WO2009036933. As also described in WO2009036933, it is particularly preferred that the ratio of the mass of VLP to RNA interference inducing molecule is between 1:100 to 100:1, more preferably 1:50 to 50:1, even more preferably 1:20 to 20:1, and most preferably in a range of 1:1 to 20:1.

The same ratios apply mutatis mutandis to the ratio of the mass of virus to RNA interference inducing molecule.

In another more preferred embodiment, the cargo molecules are enzymes, such as e.g. enzymes capable of liberating or activating cytotoxic agents that have been brought into the vicinity of the targeted tissue, for example an enzyme for pro-drug activation, such as e.g. an enzyme selected from the group consisting of carboxy-peptidases, glucuronidases and glucosidases (Bagshawe, K. D. [2009] Curr. Drug Targets 10:152-157; Chen, K.-C. [2011] Bioconjugate Chem. 22:938-948.). The cargo molecules can also be enzymes suitable for use as imaging agents, e.g. enzymes capable of catalyzing chromogenic, chemiluminescent or fluorescent reactions, such as e.g. horseradish peroxidase (HRP), luciferase, β-galactosidase and alkaline phosphatase (AP).

Further non-limiting examples of cargo molecules for imaging purposes include fluorescent proteins, such as e.g. green fluorescent protein (GFP), yellow fluorescent protein (YFP), red fluorescent protein (RFP), cyan fluorescent protein (CFP) or infrared fluorescent protein (IFP) as well as fluorescent dyes such as e.g. Fluorescein, Alexa Fluor or Cy dyes. Such cargo molecules are, amongst others, usefully as fluorescent tracers, for example in fluorescence image-guided surgery (FIGS), a medical imaging technique used to detect fluorescently labeled structures during surgery (van Dam, G. M. et al. [2011] Nat. Med. 17:1315-1319; Mondal, S. B. et a. [2014] Adv. Cancer Res. 124:171-211.).

Radioactive moieties can additionally be attached to cargo molecules for imaging, including in vivo diagnostics. Such radioactive moieties include for example the group of gamma-emitting isotopes, such as e.g. 99mTc, 123I, 125I, 111In and the group of positron emitters, such as e.g. 18F, 64Cu, 68Ga, 86Y, 124I, 89Zr. The group of beta-emitters, such as e.g. 131I, 90Y, 177Lu, 67Cu, and the group of alpha-emitters, such as e.g. 213Bi, 211At are additionally suitable for applications in radio-immuno therapy (RIT), apart from imaging or detection in vivo or in vitro.

In addition, the cargo molecules can be photosensitizers, such as e.g. bis(triethanolamine)Sn(IV)chlorin $e_6$ (SnChe$_6$). Furthermore, the cargo molecule can also be propidium iodide, which can serve as a control to ensure delivery of the cargo to the virus or VLP.

The cargo molecules can also themselves be toxic compounds, preferably small organic compounds or polypeptides. Non-limiting examples for toxic compounds include compounds selected from the group consisting of calicheamicin, neocarzinostatin, esperamicin, dynemicin, kedarcidin, maduropeptin, doxorubicin, daunorubicin, auristatin, maitansine, Ricin-A chain, modeccin, truncated *Pseudomonas* exotoxin A, diphtheria toxin and gelonin.

As discussed herein above, it is particularly preferred in accordance with one embodiment of the present invention that the VLP consists of the capsid protein VP1 of the human polyoma JC virus, i.e. that there are no other proteins present that form the VLP. In accordance with this preferred embodiment, the method of the invention thus relates to a method of producing a VLP consisting of the capsid protein VP1 of the human polyoma JO virus, carrying on its surface at least one targeting molecule that (specifically) bind(s) to a cell of interest, and further carrying one or more cargo molecules.

In a further preferred embodiment of the method of the invention, the virus or VLP further comprises additional heterologous molecules on the surface of the virus or VLP.

The term "heterologous molecule", as used herein, relates to a protein present on the surface of the virus or VLP that is not normally present on the surface of said virus. For example, the virus or VLP can carry on its surface molecules that serve as further targeting moieties or that enhance an immune response in a host after administration of the virus or VLP.

Non-limiting examples of molecules that enhance an immune response in a host include lipopolysaccharide (LPS), as well as peptides that interact with Toll-like receptors, such as e.g. TLR-4 interacting peptides that imitate a bond with LPS. Such peptides are well known in the art and have been described e.g. in Shanmugam et al. 2012, Synthetic Toll Like Receptor-4 (TLR-4) Agonist Peptides as a Novel Class of Adjuvants; PLoS ONE 7(2): e30839. The peptides described there include, as exemplary peptides, the peptides RS01 having the sequence Gln-Glu-Ile-Asn-Ser-Ser-Tyr (SEQ ID NO:7), RS02 having the sequence Ser-His-Pro-Arg-Leu-Ser-Ala (SEQ ID NO:8), RS03 having the sequence Ser-Met-Pro-Asn-Pro-Met-Val (SEQ ID NO: 9), RS04 having the sequence Gly-Leu-Gln-Gln-Val-Leu-Leu (SEQ ID NO: 10), RS05 having the sequence His-Glu-Leu-Ser-Val-Leu-Leu (SEQ ID NO: 11), RS06 having the sequence Tyr-Ala-Pro-Gln-Arg-Leu-Pro (SEQ ID NO: 12), RS07 having the sequence Thr-Pro-Arg-Thr-Leu-Pro-Thr (SEQ ID NO: 13), RS08 having the sequence Ala-Pro-Val-His-Ser-Ser-Ile (SEQ ID NO: 14), RS09 having the sequence Ala-Pro-Pro-His-Ala-Leu-Ser (SEQ ID NO: 15), RS10 having the sequence Thr-Phe-Ser-Asn-Arg-Phe-Ile (SEQ ID NO: 16), RS11 having the sequence Val-Val-Pro-Thr-Pro-Pro-Tyr (SEQ ID NO: 16) and RS12 having the sequence Glu-Leu-Ala-Pro-Asp-Ser-Pro (SEQ ID NO: 18). Further envisaged are e.g. fragments of B7 (CD86) for the direct stimulation of T cells [51].

Such additional targeting moieties can include, for example, targeting moieties bound by conventional means already known in the art, such as e.g. targeting moieties that are incorporated into the envelope of a virus or that are fused directly onto the viral-capsid, as described e.g. in Verheije and Rottier 2012. Moreover, such heterologous molecules may also be bound to the virus or VLP by the same approach as the targeting molecule, i.e. either via (i) a glycosylation of the heterologous molecule with at least one glycosyl residue recognised by the polyomavirus or polyomavirus-derived VLP; or via (ii) the use of an interaction system as described above, i.e. wherein a first interaction molecule is glycosylated with at least one glycosyl residue recognised by the polyomavirus or polyomavirus-derived VLP and a second interaction molecule is conjugated to said heterologous molecule and where the second interaction molecule is capable of interacting with the first interaction molecule.

Preferably, a virus or VLP is employed in the method of the present invention that already carries such (an) heterologous molecule, thereby obviating the need to further modify the virus/VLP.

Thus, in accordance with one preferred embodiment of the present invention, the VLP can consist of the capsid protein VP1 of the human polyoma JC virus, carrying on its surface at least one targeting molecule that binds to a cell of interest and, optionally, carrying (an) additional heterologous molecule(s) on its surface, wherein said additional heterologous molecule is not a viral capsid protein.

The present invention further relates to a polyomavirus or polyomavirus-derived VLP, wherein the virus or VLP carries on its surface at least one targeting molecule that binds to a cell of interest, and wherein the at least one targeting molecule has been bound to the surface of the virus or VLP via:

(i) a glycosylation of the at least one targeting molecule with at least one glycosyl residue, wherein said at least one glycosyl residue is recognised and bound by the polyomavirus or polyomavirus-derived VLP; or
(ii) the interaction between at least two interaction molecules, wherein a first interaction molecule is glycosylated with at least one glycosyl residue, wherein said at least one glycosyl residue is recognised and bound by the polyomavirus or polyomavirus-derived VLP; and wherein the at least one targeting molecule is conjugated to a second interaction molecule capable of interacting with the first interaction molecule.

In other words, said embodiment relates to a polyomavirus or polyomavirus-derived virus-like particle (VLP), wherein the virus or VLP carries on its surface at least one targeting molecule that binds to a cell of interest, and wherein the at least one targeting molecule is bound to the surface of the virus or VLP via:

(i) at least one glycosyl residue of the at least one targeting molecule, wherein said at least one glycosyl residue is recognised and bound by the polyomavirus or polyomavirus-derived VLP; or
(ii) the interaction between at least two interaction molecules, wherein a first interaction molecule is glycosylated with at least one glycosyl residue, wherein said at least one glycosyl residue is recognised and bound by the polyomavirus or polyomavirus-derived VLP; and wherein the at least one targeting molecule is conjugated to a second interaction molecule capable of interacting with the first interaction molecule.

The definitions and preferred embodiments provided herein above with regard to the method of the invention apply mutatis mutandis to this polyomavirus or polyomavirus-derived VLP. For example, it is explicitly envisaged that this polyomavirus or polyomavirus-derived VLP of the invention may further comprises one or more cargo molecule(s), and/or may further comprises additional heterologous molecules on its surface, as described above.

This polyomavirus or polyomavirus-derived VLP of the invention is particularly useful in research and preclinical applications, in particular applications that require the targeted delivery of specific molecules (e.g. the cargo discussed above) to target cells, as well as in medical applications, as discussed in more detail herein below. Non-limiting examples of research and preclinical applications include e.g. transfection of cells, treatment of primary cells, selective transduction in mixed-cell-cultures, tests on ex vivo material, tests on organotypic slice cultures, tests in animals etc. Further non-limiting preclinical applications include screening assays for target validation and compound testing. Moreover, the retargeted viruses or VLPs can also be immobilized, e.g. by embedding into a matrix or binding to beads, and can be employed to pull-down target cells or for interaction studies.

In a preferred embodiment of the polyomavirus or polyomavirus-derived VLP of the invention, the virus or VLP is obtained or obtainable by the method of the invention.

The present invention further relates to a composition comprising the polyomavirus or polyomavirus-derived VLP of the invention.

The term "composition", as used in accordance with the present invention, relates to a composition which comprises at least the polyomavirus or polyomavirus-derived VLP of the invention, as well as further compounds such as e.g. molecules capable of altering the characteristics of the polyomavirus or polyomavirus-derived VLP of the invention thereby, for example, stabilizing, delaying, modulating and/or activating its function or, alternatively, at least one container. The composition may be in solid, liquid or gaseous form and may be, inter alia, in the form of (a) powder(s), (a) tablet(s), (a) solution(s) or (an) aerosol(s).

The composition may further comprise more than one type of polyomavirus or polyomavirus-derived VLP in accordance with the invention. In that case, it is particularly preferred that the the polyomavirus or polyomavirus-derived VLP comprised in the composition comprises different targeting molecules, different additional heterologous molecules on the surface of the virus or VLP and/or different cargo molecules, as defined above.

In one preferred embodiment, the composition is a pharmaceutical composition.

In accordance with the present invention, the term "pharmaceutical composition" relates to a composition for administration to a patient, preferably a human patient. The pharmaceutical composition of the invention comprises the compound(s) recited above. The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutically acceptable carriers are well known in the art and include sodium chloride solutions, such as phosphate-buffered sodium chloride solutions, water, emulsions, such as oil/water emulsions, various types of wetting agents, sterile solutions, organic solvents etc. Such pharmaceutically acceptable carriers often contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) peptides, e.g., polyarginine or tripeptides; proteins, such as serum albumin, gelatin, or further immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; sugar alcohols such as mannitol or sorbitol; counter-ions such as sodium; and/or non-ionic surfactants such as polysorbates, poloxamers, or PEG. Also chitosan may be comprised in the pharmaceutical composition, e.g. for use in delaying the release of the virus or VLP upon administration.

The pharmaceutical composition may comprise further agents depending on the intended use of the pharmaceutical composition, such as e.g. antitumoral agents for use in the treatment of tumors.

Administration of pharmaceutical compositions of the invention may be effected by different ways, e.g., by intravenous, intraperitoneal, subcutaneous, intramuscular, intradermal, intranasal or intrabronchial administration. Accordingly, it is preferred that the pharmaceutically acceptable carrier is a carrier suitable for these modes of administration. Most preferably, the carrier is a solution that is isotonic with the blood or tissue fluid of the recipient. Compositions comprising such carriers can be formulated by well known conventional methods. Generally, the formulations are prepared by contacting the components of the pharmaceutical composition uniformly and intimately with liquid carriers or finely divided solid carriers or both. Then, if necessary, the product is shaped into the desired formulation. Preferred modes of administration of the pharmaceutical compositions of the invention are by intravenous, intramuscular or intraperitoneal injection, as well as by delivery via an aerosol or a hydrogel, such as e.g. chitosan-based hydrogels.

The pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. The pharmaceutical composition may be for administration once or for a regular administration over a prolonged period of time. Generally, the administration of the pharmaceutical composition should be in the range of for example 1 µg/kg of body weight to 50 mg/kg of body weight for a single dose, preferably around 0.5 mg/kg of body weight. However, a more preferred dosage might be in the range of 10 µg/kg to 20 mg/kg of body weight, even more preferably 100 µg/kg to 10 mg/kg of body weight and even more preferably 500 µg/kg to 5 mg/kg of body weight for a single dose.

The components of the pharmaceutical composition to be used for therapeutic administration must be sterile. Sterility is readily accomplished, for example, by filtration through sterile filtration membranes (e.g., 0.2 µm membranes).

The pharmaceutical composition may be particularly useful for the treatment of tumors and/or diseases amenable to treatment with gene therapy approaches, as disclosed below.

In another preferred embodiment, the composition of the invention is a diagnostic composition.

In accordance with the present invention, the term "diagnostic composition" relates to compositions for diagnosing whether a patient is suffering from a particular disease, for example from cancer. For example, by labeling the virus or VLPs with a detectable moiety (e.g. as discussed above) and targeting it to cancer cell-specific marker molecules, the presence and location of cancerous cells within a patient may be detected. The diagnostic compositions of the present invention can be used in in vivo as well as in in vitro or ex vivo diagnostic experimental designs well known in the art. The diagnostic composition of the invention comprises at least an polyomavirus or polyomavirus-derived VLP according to the invention. The diagnostic composition may further comprise appropriate buffer(s) etc.

The components of the pharmaceutical or diagnostic composition can be packaged in a container or a plurality of containers, for example, sealed ampoules or vials, as an aqueous solution or as a lyophilized formulation for reconstitution. Preferably, the components of the composition are packaged with instructions for use. As an example of a lyophilized formulation, 10-ml vials are filled with 5 ml of 1% (w/v) or 10% (w/v) aqueous solution, and the resulting mixture is lyophilized. A solution for use is prepared by reconstituting the lyophilized compound(s) using either e.g. water-for-injection for therapeutic uses or another desired solvent, e.g. a buffer, for diagnostic purposes. Preservatives and other additives may also be present such as, for example, antimicrobials, anti-oxidants, chelating agents, and inert gases and the like.

The present invention also relates to the polyomavirus or polyomavirus-derived VLP of the invention or the composition of the invention for use as a medicament.

For example, the virus or VLP of the invention can be employed to deliver cargo molecules, such as modulatory or immunogenic nucleic acids as discussed herein above, to target cells of interest. Such cargo molecules may e.g. serve for gene therapy approaches, for RNA interference approaches, as well as for DNA-based tumour vaccination approaches.

Gene therapy is based on introducing therapeutic nucleic acid constructs, typically DNA constructs, for correcting a genetic defect into germ line cells by ex vivo or in vivo techniques. Thus, gene therapy is currently one of the most important applications of gene transfer. Suitable methods for in vitro or in vivo gene therapy are described in the literature and are known to the person skilled in the art [6, 52-54]. Non-limiting examples of diseases that are suitable for being treated with gene therapy include genetic disorders like severe combined immune deficiency (ADA-SCID), chronic granulomatous disorder (CGD) or haemophilia. In addition, acquired diseases that may be treated by gene therapy include, without being limiting, cancer (e.g. lung cancer, breast cancer, colorectal cancer), neurodegenerative diseases (e.g. Parkinson's Disease or Huntington's Disease) and other acquired disorders such as viral infections, heart disease and diabetes.

RNA interference approaches are of particular interest for use in the treatment of diseases caused by the expression of nucleic acids from a pathogenic organism, or by the aberrant expression of an endogenous nucleic acid, i.e. an expression in increased amounts or the unwanted expression thereof. RNA interference can be employed to down-regulate the expression of such nucleic acids, as described e.g. in WO2009036933. For example, VLPs or virus could deliver RNAi effectors that inhibit expression of viral genes, including, without being limiting, HIV-1 (human immunodeficiency virus), Hepatitis, KSHV (Kaposi's sarcoma-associated herpesvirus), EBV (Epstein-Barr virus) and also Polyoma JC virus.

DNA-based tumour vaccination approaches are also well known in the art and have been described, e.g. in Fioretti et al. 2010 [55]. DNA vaccination is commonly used to induce an immune response of the host to foreign genetic material of e.g. viruses, bacteria and parasites. To minimize side immunological effects, resistance-cassettes and ori sequences for microbiological amplification of the plasmid have to be reduced to a minimum. One particularly suited approach encompasses the use of MIDGE vectors, which are minimized DNA cassettes, the ends of which have been closed by hairpins to result in linearized, monomolecular DNAs [56]. Besides utilization of such minimalized vectors in gene therapy settings as mentioned above, they are in particular useful for e.g. DNA driven tumor vaccination approaches.

The present invention further relates to a kit comprising the polyomavirus or polyomavirus-derived virus-like particle (VLP) of the invention, or the composition of the invention.

Whereas the term "kit" in its broadest sense does not require the presence of any other compounds other than the recited components, the term "comprising", in the context of the kit of the invention, denotes that further components can be present in the kit. Non-limiting examples of such further components include preservatives, buffers, enzymes etc.

Where several components are comprised in the kit, the various components of the kit may be packaged in one or more containers such as one or more vials. Consequently, the various components of the kit may be present in isolation or combination. The containers or vials may, in addition to the components, comprise preservatives or buffers for storage and buffers for assembly. In addition, the kit contains instructions for use.

This kit finds numerous applications, in particular in research and medicine, as detailed above. It is particularly preferred that the kit is a kit for the delivery of cargo molecules to target cells.

Unless otherwise defined, all technical and scientific terms used herein have the same meaning as commonly understood by one of ordinary skill in the art to which this invention belongs. In case of conflict, the patent specification, including definitions, will prevail.

All the sequences accessible through the Database Accession Numbers cited herein are within the scope of the present invention and also include potential future updates in the database, in order to account for future corrections and modifications in the entries of the respective databases, which might occur due to the continuing progress of science.

All amino acid sequences provided herein are presented starting with the most N-terminal residue and ending with the most C-terminal residue (N→C), as customarily done in the art, and the one-letter or three-letter code abbreviations as used to identify amino acids throughout the present invention correspond to those commonly used for amino acids.

Regarding the embodiments characterised in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 10, 9 and 6 is clearly and unambiguously envisaged in view of the claim structure. The same applies for example to the combination of claims 12, 9 and 7, or the combination of claims 12, 9 and 4, etc.

THE FIGURES SHOW

FIG. 1: General structure of a JCV VLP and attachment of targeting proteins.

The VP1 protein dissociates to oligomeric fractions after addition of EGTA and DTT (15 mM each). In the presence of the CAG-GFP expression cassette, EGTA and DTT are removed by dialysis while adding $CaCl_2$ to the VP1, resulting in capsid formation and incorporation of the DNA. In the schematic at the bottom left, the HER2/neu scFv fragment is crosslinked onto the capsid by a polylinker (NHS-PEG6-Maleimid) via established methods, resulting in a covalent sulfhydryl- and isopeptide-bond. In the schematic at the bottom right, the HER2/neu-Streptavidin scFv is bound via LSTc-Biotin onto the viral capsid.

Figure 2:
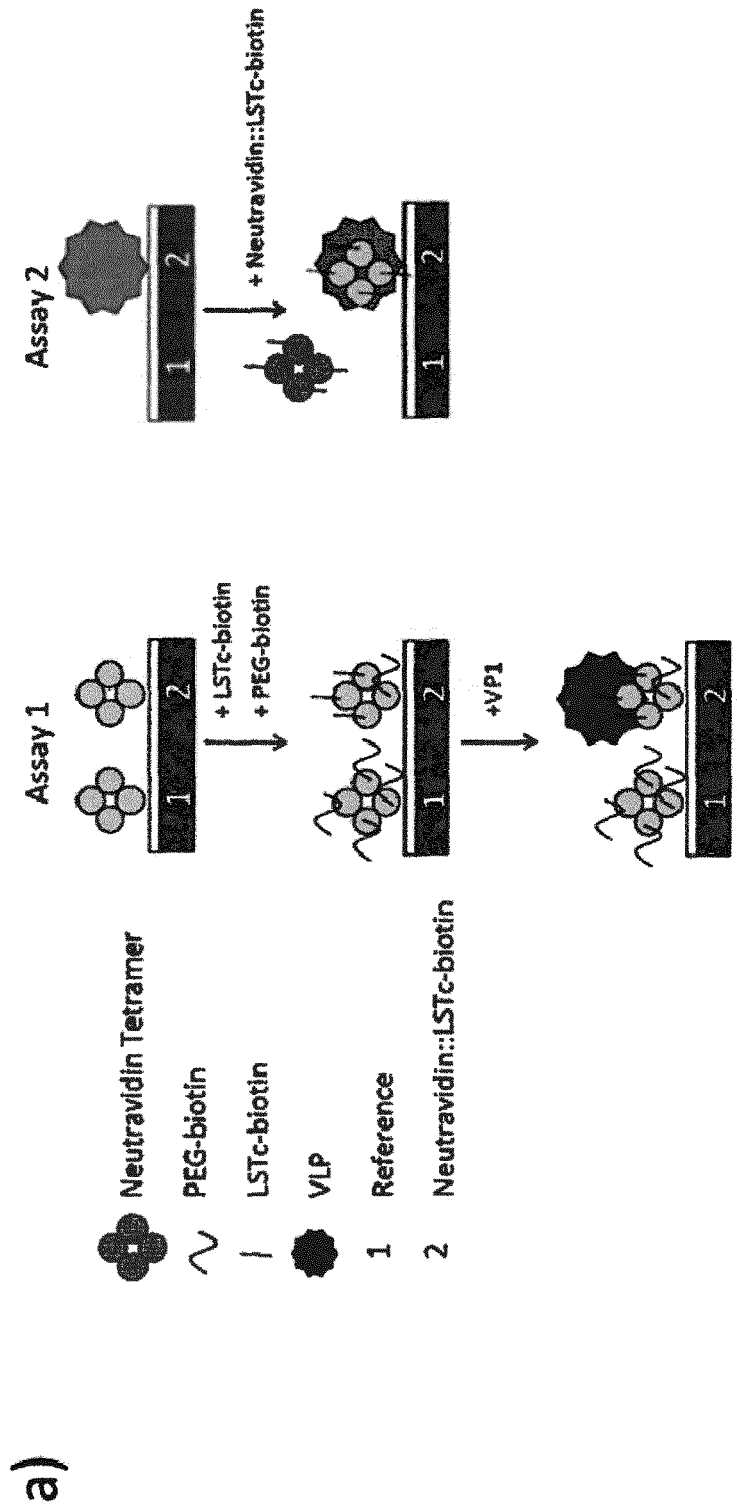
Figure 2:
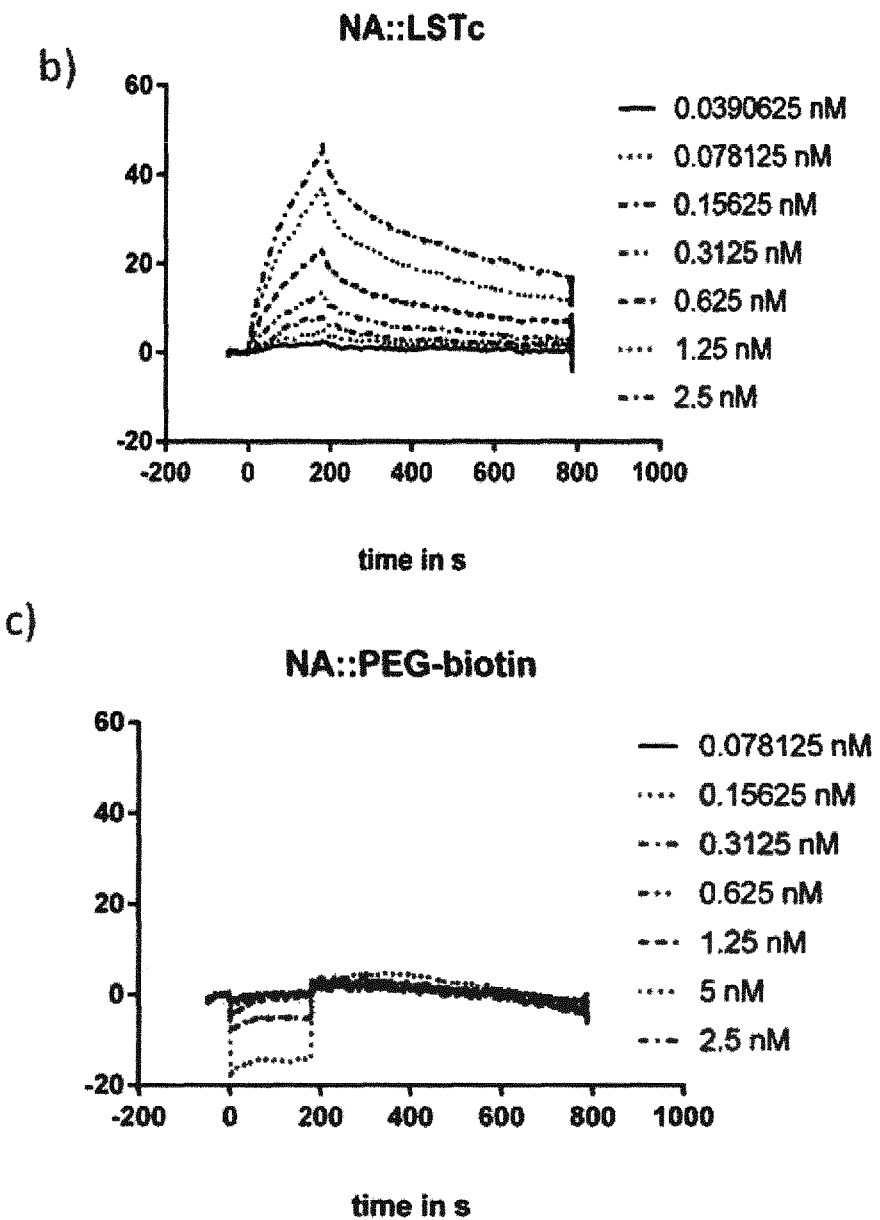

FIG. 2: Schematic drawing of SPR (surface plasmon resonance) setting to study the affinity of LSTc to the surface of a VLP.

a) General setup of SPR-measurements: Assay 1 depicts a setup wherein LSTc-Biotin is immobilized and the VP1-VLP is present in the mobile phase and only becomes immobilized upon binding of the VP1-VLP onto the immobilized LSTc. Assay 2 shows a setup wherein the VP1-VLP is immobilized and Neutravidin::LSTc-Biotin is present in the mobile phase and becomes immobilized upon binding of LSTc onto the immobilized VP1-VLP. b) Injection of Neutravidin::LSTc-Biotin complexes to immobilized VP1; the highest concentration used was 5 µM. The binding pattern obtained is characteristic for an interaction of high avidity. c) Control-experiment of Neutravidin::PEG.Biotin as mobile phase analyte, which shows that no interaction was detected with immobilized VP1.

Figure 3:
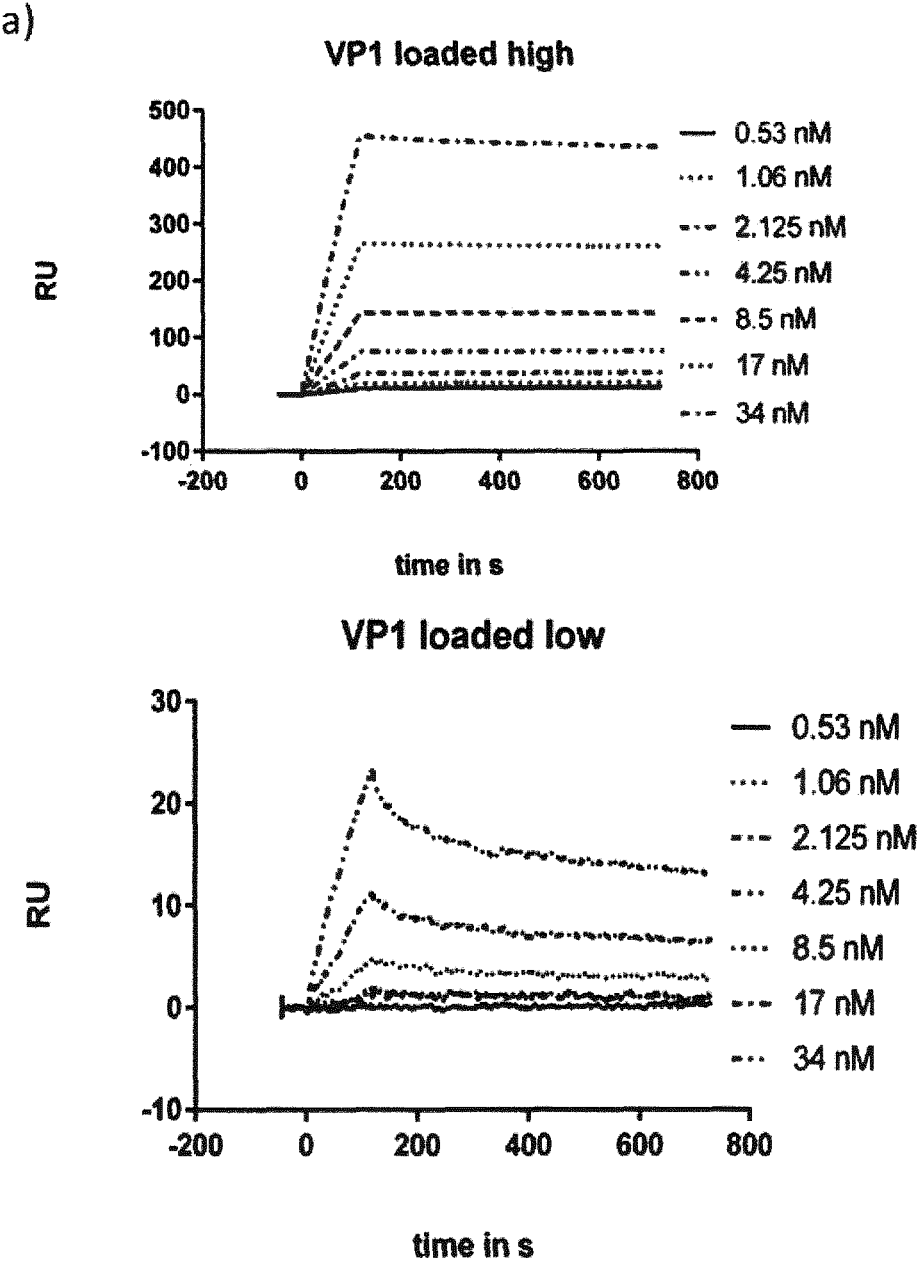
Figure 3:
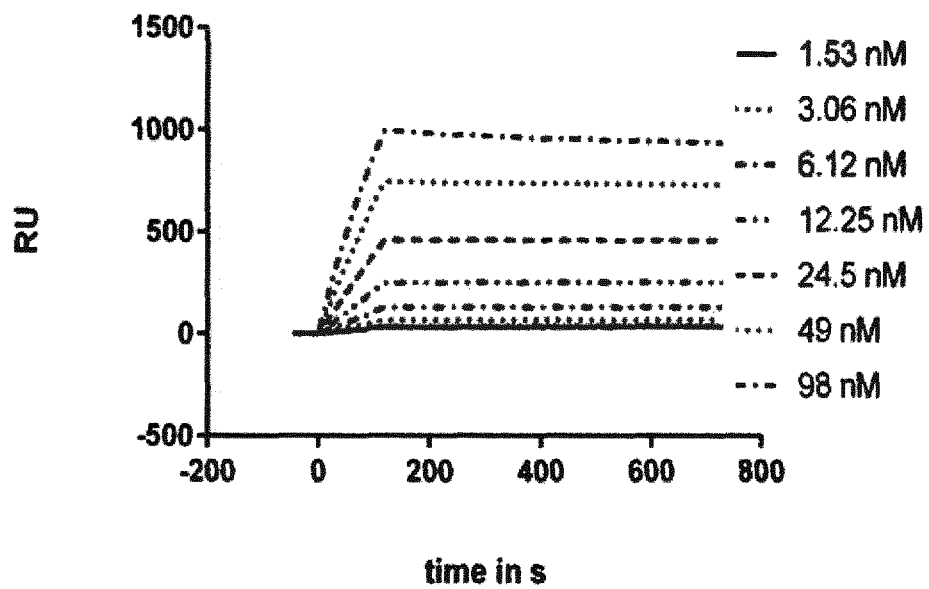
Figure 3:
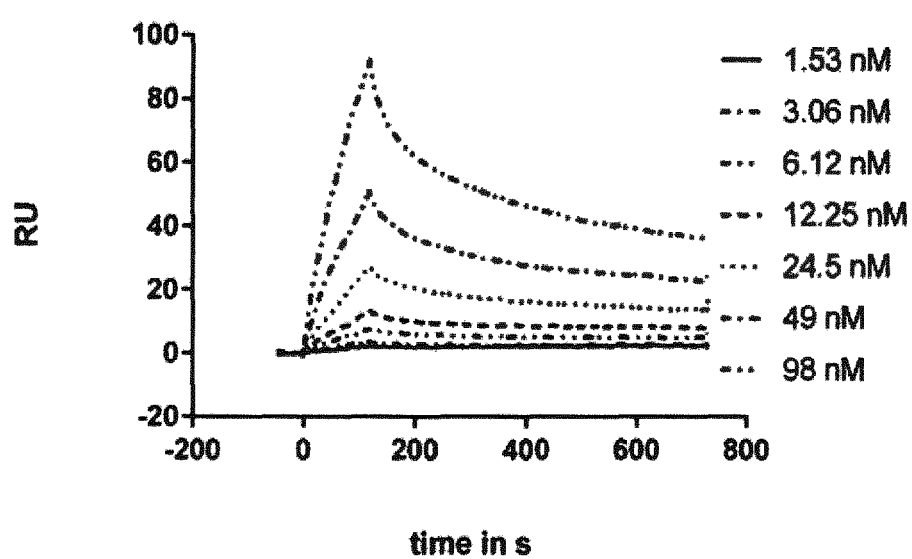

FIG. 3: SPR measurements to demonstrate the affinities of LSTc to recombinant VLPs and JCV capsomers.

a) Neutravidin::LSTc-Biotin matrix-surface with high and low loading density. Binding of siRNA-loaded VLPs was monitored with a concentration of up to 32 nM. Signal pattern and stability show exponential behaviour, underpinning a strong avidity effect. b) Neutravidin::LSTc-Biotin matrix-surface with high and low loading density. Binding of siRNA-loaded VLPs was monitored with a concentration of up to 98 nM. Signal pattern and stability show again an exponential behaviour, underpinning a strong avidity effect.

Figure 4:
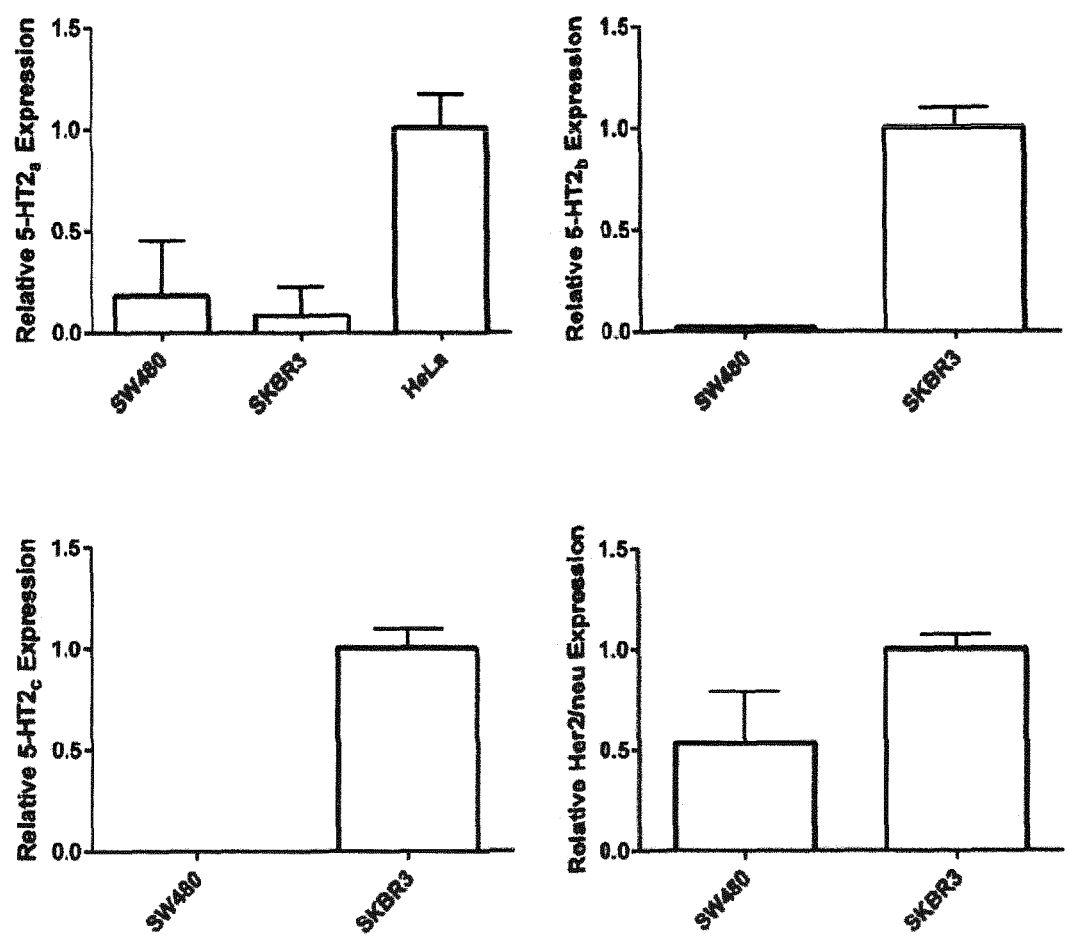

FIG. 4: 5HT2R (serotonin receptor) expression analysis on human cell lines to investigate HT2R subtype (a, b, or c) expression on relevant human cell lines.

The bars show qRT-PCR analysis results obtained for the cell lines used (Hela, SW480 and Skbr3) and depict the relative expression of the 5-HT2 serotonin receptor isoforms a, b, and c as well as the relative expression of HER2/neu.

Figure 5:
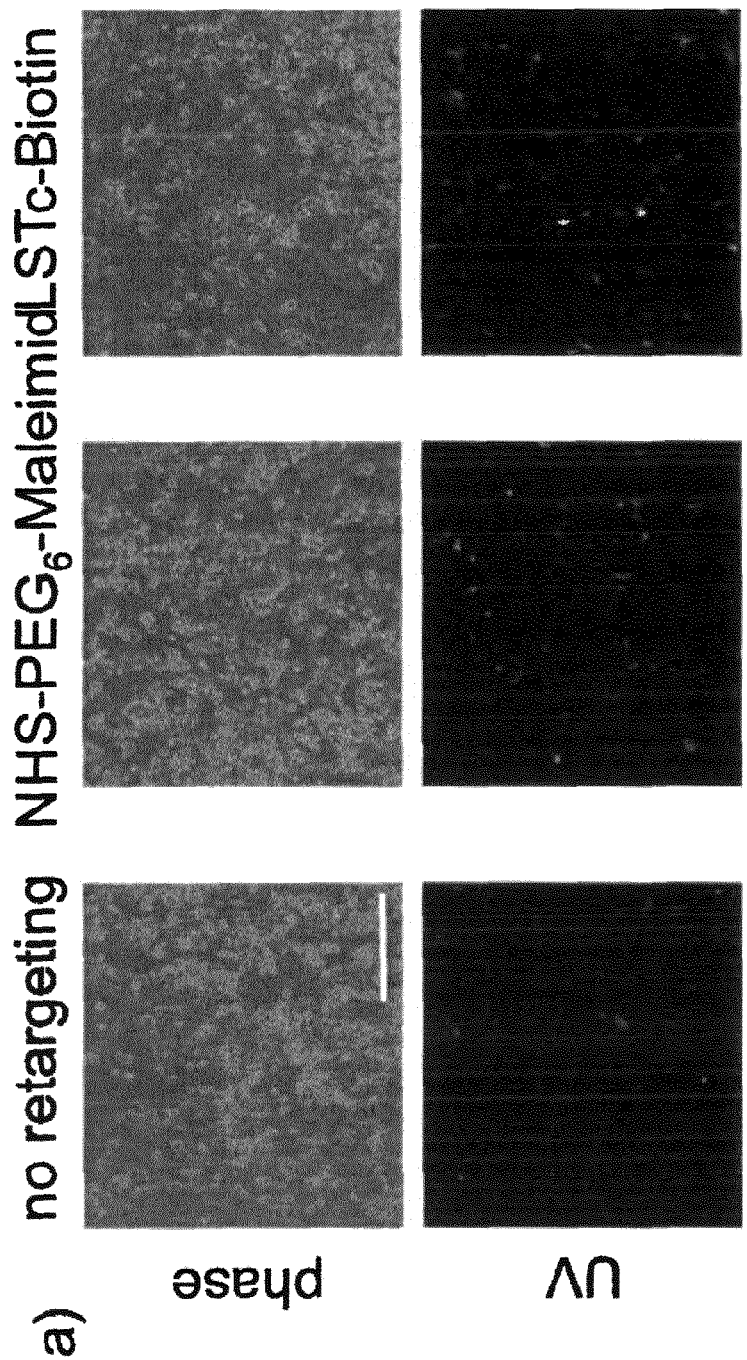
Figure 5:
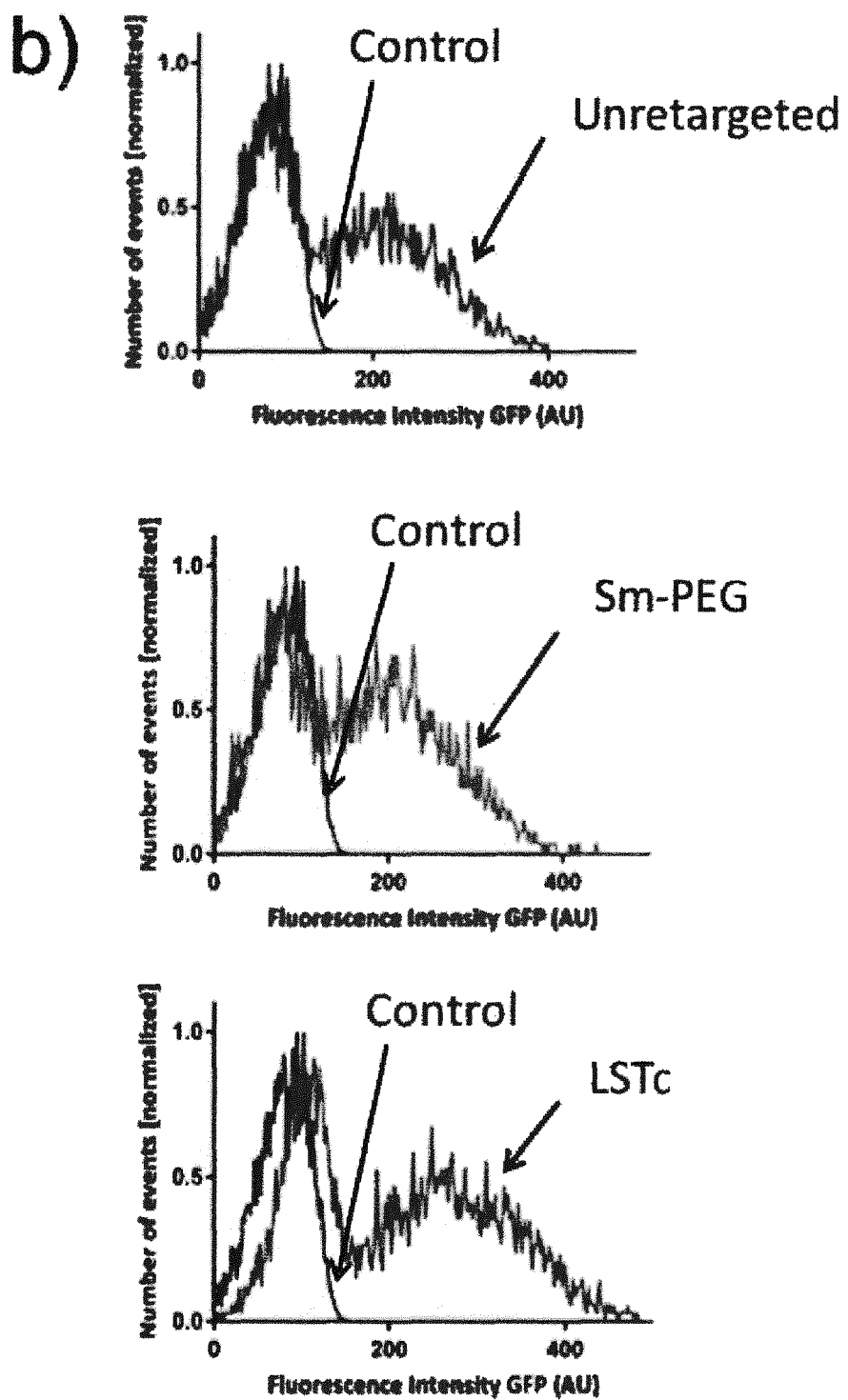

FIG. 5: Transduction of SKBR3 cells.

a) Phase contrast- and UV-pictures of SKBR3 for GFP-expression after transduction with CAG-GFP expression cassette loaded native VLPs (depicted as "no retargeting" or "unretargeted" on the left), and after transduction with CAG-GFP expression cassette loaded retargeted VLPs. Crosslinking to HER2/neu scFv was performed with NHS-PEG$_6$-Maleimid, HER2/neu-Streptavidin scFv was bound onto the VLPs by LSTc-Biotin (scale bar: 200 µm, exposure time 1 sec). b) FACS analysis of SKBR3 showed different percentages of GFP-positive populations by usage of unretargeted VLPs and retargeted VLPs (no retargeting: 50%, NHS-PEG$_6$-Maleimid: 55%, LSTc-Biotin: 55%).

Figure 6:
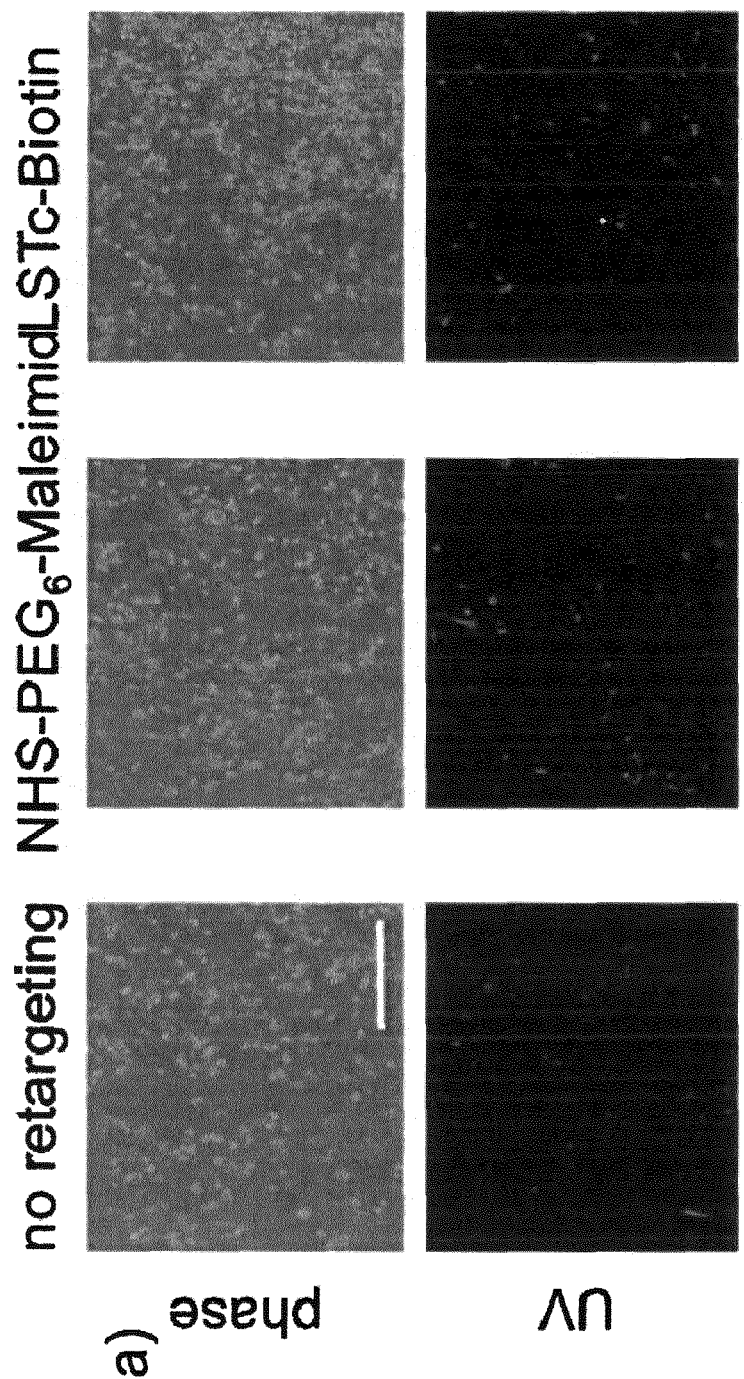
Figure 6:
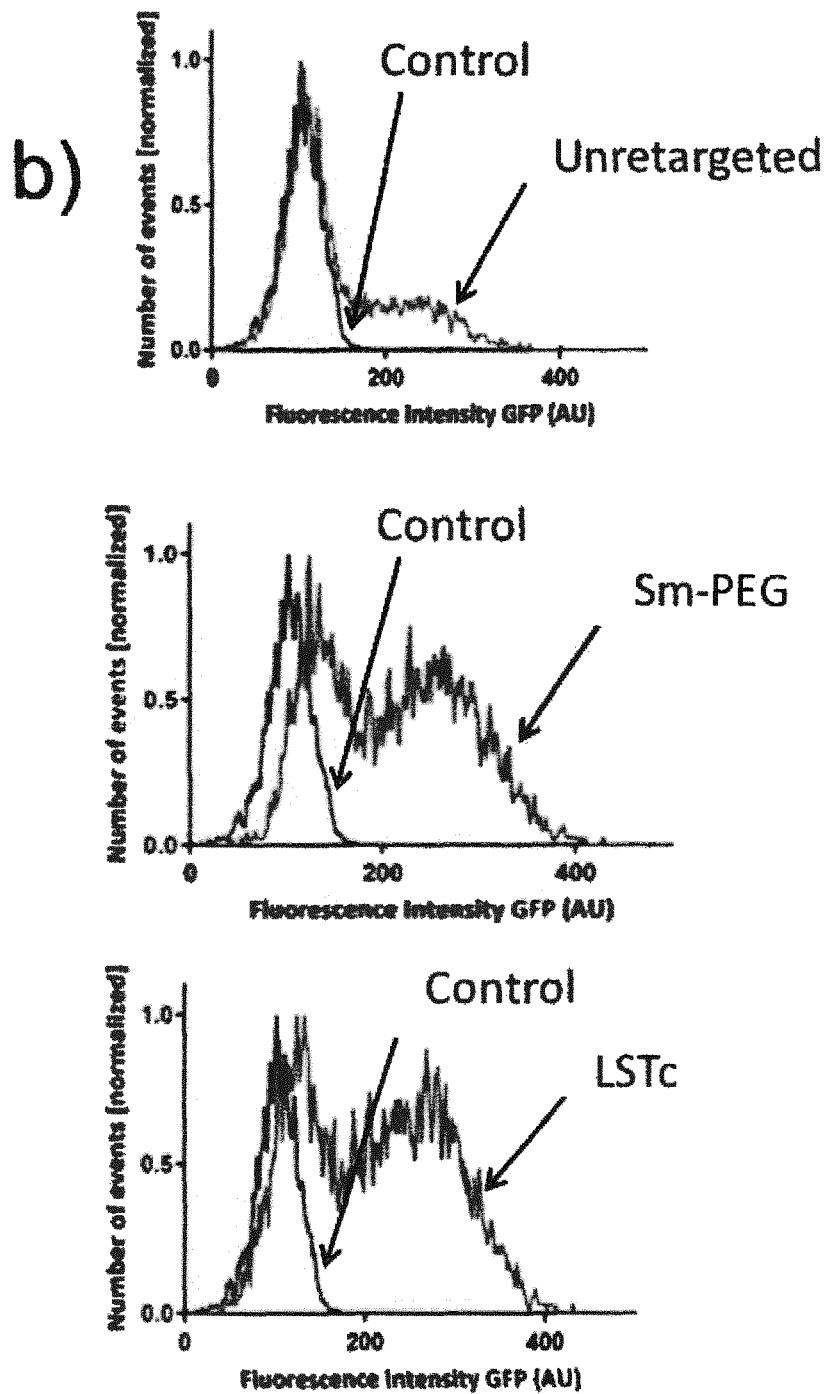

FIG. 6: Transduction of SW480 cells.

a) Phase contrast- and UV-pictures of SW480 for GFP-expression after transduction with CAG-GFP expression cassette loaded native VLPs (depicted as "no retargeting" or "unretargeted" on the left), and after transduction with CAG-GFP expression cassette loaded retargeted VLPs. Crosslinking to HER2/neu scFv was performed with NHS-PEG$_6$-Maleimid, HER2/neu-Streptavidin scFv was bound onto the VLPs by LSTc-Biotin (scale bar: 200 µm, exposure time 1 sec). b) FACS analysis of SW480 showed different percentages of GFP-positive populations by usage of unretargeted VLPs and retargeted VLPs (no retargeting: 20%, NHS-PEG$_6$-Maleimid: 55%, LSTc-Biotin: 65%).

The following examples illustrate the invention:

EXAMPLE 1: MATERIAL AND METHODS

GFP-Expression Cassette Generation

The CAG-GFP expression construct was amplified from the pAAV-CAG-GFP plasmid (Addgene #28014) (for 5"-3" GATCGTACCATTGACGTCAATAATG (SEQ ID NO: 19), rev 5'-3' TCTCCCCCTGAACCTGAAAC (SEQ ID NO: 20)). The amplicon was transferred via TA-cloning into the pGEM®-T Easy vector (Promega). The woodchuck hepatitis virus posttranslational regulatory element (WPRE) sequence was removed by PCR-amplification of the plasmid, followed by self-ligation (for 5"-3"p-TCGA-TACCGTCGACCCG (SEQ ID NO: 21), rev 5"-3" p-TTATCGATAAGCTTGATATCGAATTC (SEQ ID NO: 22)). The linear expression cassette was generated by SacI/SphI digestion, giving rise to the 1946 bp construct. Linear DNA was purified with QIAquick® gel extraction kit (Qiagen) according to the manufacturer's protocol.

VLP Production and Loading

JC polyomavirus-like particles were generated as described elsewhere [57]. For transduction the desired amount of VLPs was incubated in disassembly buffer (10 mM HEPES [pH 7.4], containing 150 mM NaCl and 15 mM EGTA and DTT each) at room temperature (RT) for 30 min. Per 25 µg of VLPs, 500 ng in total of the linearized GFP-expression construct were added and incubated for another 30 min at RT. VLPs were reassembled by dialyzing against 5 L of reassembly buffer (10 mM HEPES [pH 7.4], containing 150 mM NaCl and 1 mM $CaCl_2$) at 4° C. under constant stirring over night.

ScFv Production and Cross-Linking

HER2/neu ScFv DNA was ordered from Geneart based on the sequence published elsewhere [58, 59] as a codon-optimized construct for expression in *Pichia pastoris* and transferred as XbaI/XhoI amplicon into the pPICZαA-vector (Invitrogen). Streptavidin was fused by overlap extension PCR from the pTSA-c plasmid (Addgene #17329) to the c-terminus of the scFv. The linearized plasmids were transformed into the humanized *P. pastoris* SuperMan$_5$ strain (his$^+$) and grown under standard conditions. In brief, expression of the construct was performed in BMMH full medium at 28° C. and 160 rpm with feeding of methanol to a final concentration of 1% every 24 h. After 3 days, the supernatant was harvested by centrifugation (30 min, 10000×g, RT) and filtered through a 0.45 µm filter. HER2/neu scFV and HER2/neu-Streptavidin scFv were enriched from the supernatant by immobilized metal ion affinity chromatography (IMAC). ScFv-containing eluate fractions were dialyzed over night against reassembly buffer at 4° C. under constant stirring and subsequently concentrated by usage of a Vivaspin column (MWCO 5 kDa) at 4° C. to the desired concentration of 0.5-1 mg/mL.

For cross-linking with HER2/neu scFv, the desired amount of HER2/neu ScFv was incubated for 1 h at RT with DTT to a final concentration of 5 mM to reduce its N-terminal cysteine for cross-linking. Excess DTT was removed by gel filtration (PD10 desalting column) and HER2/neu ScFv was concentrated by a Vivaspin column (MWCO 5 kDa).

The desired amount of CAG-GFP loaded VLPs were incubated with NHS-PEG$_6$-Maleimide (Invitrogen, Dreieich, Germany) according to the manufacturer's protocol. After 1 h of incubation at RT, the remaining NHS-PEG$_6$-Maleimide was removed by gelfiltration (PD10 desalting column equilibrated with reassembly buffer) and the coated VLPs were concentrated by usage of a Vivaspin column (MWCO 30 kDa).

The coated VLPs were then incubated with the reduced HER2/neu ScFv with a final ratio of 1:5 (10 µg VLPs/50 µg scFv) for 1 h at RT before they were used for transduction.

For cross-linking of HER2/neu-Streptavidin via the method of the invention, 300 µg of HER2/neu scFv (0.5 mg/mL) were incubated for 1 h at RT with lactoseries tetrasaccharide c (LSTc)-Biotin with a final concentration of 160 µM. Excess LSTc-Biotin was removed by gelfiltration (PD10 desalting column) and the LSTc-Biotin-conjugated HER2/neu-Streptavidin scFv was concentrated by a Vivaspin column (MWCO 5 kDa). The VLPs were incubated with this LSTc-Biotin-conjugated HER2/neu-Streptavidin scFv with a final ratio of 1:2 (10 µg VLPs/20 µg scFv) for 1 h at RT before they were used for transduction.

Transduction Experiments

For VLP transduction experiments, the cell lines SKBR3 and SW480 were seeded in DMEM medium containing FCS (10%) and Pen/Strep (1%) at a density of 25.000 cells/well in a 24-well plate and grown over night under standard culture conditions. Prior to transduction, the medium was changed to FCS-free DMEM containing Pen/Strep (1%). Per well, 25 µg of wt, NHS-PEG$_6$-Maleimid HER2/neu scFv, or LSTc-Biotin HER2/neu-Streptavidin scFv coated VLPs, packaged with 500 ng CAG-GFP expression cassette, were added and incubated for 24 h. Afterwards, the medium was removed and FCS-containing DMEM was added and the cells were incubated for another 48 h. 3 day post transduction, cells were analysed for GFP-expression by microscopy and FACS.

Quantitative PCR Analysis

Total RNA was isolated via Phenol/Chloroform extraction according to manufacture protocol (Trizol, Thermo Fisher Scientific, Waltham Mass., USA). RNA was measured by synergy system (Biotek, Winooski Vt., USA), 1000 ng of total RNA was reverse transcribed using Sensifast cDNA Synthesis Kit (Bioline, London, UK) and 1 µL of the obtained cDNA was used for quantitative analysis on ABI StepOnePlus system (Applied biosystems, Waltham Mass., USA). Relative expression of 5-HT2$_a$, 5-HT2$_b$ and 5-HT2$_c$ was calculated via ΔΔC$_T$-method using β2M as housekeeping gene. For analysis of the 5-HT2$_a$ isoform, HeLa cells were used for normalization due to the low expression of this isoform in SKBR3- and SW480-cells.

| Primer | sequence fwd | sequence rev | Reference |
|---|---|---|---|
| b2m | TGTGCTCGCGCTACT CTCTCT (SEQ ID NO: 23) | CGGATGGATGAAACC CAGACA (SEQ ID NO: 24) | – |
| Ht2a | AACTCCAGAACTAAG GCATTT (SEQ ID NO: 25) | CTTAAAGACCTTCGA ATCGTC (SEQ ID NO: 26) | [60] |
| Ht2b | CACGGGCTACAGCAT TCATCA (SEQ ID NO: 27) | CCAAAACGTTCCTTT GTCAGC (SEQ ID NO: 28) | – |
| Ht2c | CCGAGTCCGTTTCTC GTCTAG (SEQ ID NO: 29) | GATGGCGTCAGTTGG CCTATG (SEQ ID NO: 30) | – |
| Her2/ neu | CCTCTGACGTCCATC GTCTC (SEQ ID NO: 31) | CGGATCTTCTGCTGC CGTCG (SEQ ID NO: 32) | [61] |

Row Cytometry

Cells were trypsinized and fixated for 20 min at 4° C. with 2% PFA in PBS. Flow cytometry was performed using BD LSR II instrument (BD Biosciences), filters employed for GFP were (505LP-BP530/30) using a 488 nm laser. Data analysis was performed using flowing software, the flow Core Bioconductor package and GraphPad software (GraphPad Prism version 7.00 for Windows, GraphPad Software, La Jolla Calif. USA). For histograms gated and binned data were extracted from the flowing software, normalized by % max (bin value/max value from all binned data) and plotted using GraphPad.

EXAMPLE 2: RETARGETING OF VLPS

The recombinantly expressed VP1 of human JC polyomavirus was purified to homogeneity as described elsewhere. Upon purification, the VLPs were subjected to an in vitro DNA packaging process. VLPs are known to dissociate into smaller mono- and oligomers (FIG. 1) in the presence of reducing and chelating agents (DTT and EGTA). These fractions can be reassembled to functional VLPs in the presence of CaCl$_2$ while withdrawing the added DTT and EGTA by dialysis. During this process, cargo molecules like nucleic acids can be added, giving rise to loaded VLPs. In the present experiments, VLPs were used which were loaded with a CAG-GFP expression cassette.

To alter the tropism of the VLPs, the retargeting approach of the present invention was employed, which is based on the VLPs ability to bind LSTc. By fusion of LSTc to Biotin, it was possible to attach an scFv-Streptavidin fusion construct onto the VLP.

In a comparative experiment, an scFv was covalently link onto the surface of the particles. For this approach, two lysine-residues (K60 and K164), located in the flexible loops of the outer surface of the VLPs, were utilized. Moreover the scFv carried a c-terminal cystein, which enabled the use of a polylinker with two different functional groups at each end (SM-$PEG_6$-Maleimide) to connect the lysine-residues with the scFv.

The thus retargeted VLPs were then used for transducing HER2/neu positive mammalian breast- and colorectal-cancer cell lines (SKBR3 and SW480).

EXAMPLE 3: ANALYSIS OF 5-HT2 SEROTONIN RECEPTOR EXPRESSION AND HER2/NEU EXPRESSION

Because uncoated VLPs require the 5-HT2 serotonin receptor to transduce cells, the expression of the three 5-HT2 isoforms a, b and c in the cells SKBR3 and SW480 used herein was initially analyzed (FIG. 4). HeLa cells were used as control for the 5-HT2a isoform, since SKBR3 and SW480 show only low expression of this isoform (one-fifth to one-tenth of HeLa). The 5-HT2b isoform shows a several hundred-fold overexpression in SKBR3 cells when compared to HeLa cells. Therefore, SKBR3 was chosen for normalization of the data. Corresponding normalization of the expression-rate of the 5-$HT_{2b}$ isoform in HeLa, SW480 and Raji cells resulted in relative values close to the background level. The same result was obtained with the 5-HT2c isoform.

Analysis of the expression of Her2/neu in SW480 and SKBR3 cells additionally confirmed the presence of this receptor on the cells employed herein. Both SKBR3 and SW480 show high expression of the receptor, whereas SKBR3 showed a two-fold higher expression rate.

EXAMPLE 4: TRANSDUCTION OF THE HER2/NEU POSITIVE CELL LINES SKBR3 AND SW480 WITH VLPS

Using VLPs that were not retargeted (i.e. "unretargeteted VLPs") but were loaded with the CAG-GFP expression cassette, it was possible to transduce SKBR3 and SW480 cells (FIG. 5, 6, left side of the Figures). FACS analysis underpinned this result while revealing different values of GFP-positive cells for the tested cell-lines (SKBR3: 50%, SW480 20%).

To more efficiently transduce HER2/neu positive cell lines, the serotonergic tropism of the JCV derived VLPs was altered. Using the VLPs retargeted as described in Example 2, it was possible to transduce SW480 and SKBR3 cells with the used CAG-GFP expression cassette with both retargeting approaches (FIG. 5, 6, middle and right side of the Figures). These findings were supported by FACS analysis (NHS-$PEG_6$-Maleimid: SKBR3: 55%, SW480: 55%; LSTc-Biotin: SKBR3: 55%, SW480: 65%).

Because SKBR3 cells express not only Her2/neu, but also the native JCV receptor, both unretargeteted and retargeted VLPs of JCV can transduce these cells. However, SW480 cells only express Her2/neu and, consequently, a significant increase in transduction efficiency was observed in the above described experiments. Moreover, the retargeting approach of the present invention not only represents a less cumbersome and less time consuming method of retargeting, it also resulted in a further increase in efficiency (i.e. an increase from 20% to 65% in SW480 cells).

REFERENCES

[1] Y. P. Liu, J. T. Westerink, O. ter Brake, B. Berkhout, RNAi-inducing lentiviral vectors for anti-HIV-1 gene therapy, Methods in molecular biology, 721 (2011) 293-311.

[2] S. Weinstein, I. A. Toker, R. Emmanuel, S. Ramishetti, I. Hazan-Halevy, D. Rosenblum, M. Goldsmith, A. Abraham, O. Benjamini, O. Bairey, P. Raanani, A. Nagler, J. Lieberman, D. Peer, Harnessing RNAi-based nanomedicines for therapeutic gene silencing in B-cell malignancies, Proceedings of the National Academy of Sciences of the United States of America, 113 (2016) E16-22.

[3] J. L. Gori, P. D. Hsu, M. L. Maeder, S. Shen, G. G. Welstead, D. Bumcrot, Delivery and Specificity of CRISPR-Cas9 Genome Editing Technologies for Human Gene Therapy, Human gene therapy, 26 (2015) 443-451.

[4] L. Naldini, Gene therapy returns to centre stage, Nature, 526 (2015) 351-360.

[5] R. Sharma, X. M. Anguela, Y. Doyon, T. Wechsler, R. C. DeKelver, S. Sproul, D. E. Paschon, J. C. Miller, R. J. Davidson, D. Shivak, S. Zhou, J. Rieders, P. D. Gregory, M. C. Holmes, E. J. Rebar, K. A. High, In vivo genome editing of the albumin locus as a platform for protein replacement therapy, Blood, 126 (2015) 1777-1784,

[6] R. Waehler, S. J. Russell, D. T. Curiel, Engineering targeted viral vectors for gene therapy, Nature reviews. Genetics, 8 (2007) 573-587.

[7] E. Blanco, H. Shen, M. Ferrari, Principles of nanoparticle design for overcoming biological barriers to drug delivery, Nature biotechnology, 33 (2015) 941-951.

[8] B. Assetta, M. S. Maginnis, I. Gracia Ahufinger, S. A. Haley, G. V. Gee, C. D. Nelson, B. A. O'Hara, S. A. Allen Ramdial, W. J. Atwood, 5-HT2 receptors facilitate JC polyomavirus entry, Journal of virology, 87 (2013) 13490-13498.

[9] G. F. Elphick, W. Querbes, J. A. Jordan, G. V. Gee, S. Eash, K. Manley, A. Dugan, M. Stanifer, A. Bhatnagar, W. K. Kroeze, B. L. Roth, W. J. Atwood, The human polyomavirus, JCV, uses serotonin receptors to infect cells, Science, 306 (2004) 1380-1383.

[10] U. Neu, M. S. Maginnis, A. S. Palma, L. J. Stroh, C. D. Nelson, T. Feizi, W. J. Atwood, T. Stehle, Structure-function analysis of the human JC polyomavirus establishes the LSTc pentasaccharide as a functional receptor motif, Cell host & microbe, 8 (2010) 309-319.

[11] L. J. Stroh, M. S. Maginnis, B. S. Blaum, C. D. Nelson, U. Neu, G. V. Gee, B. A. O'Hara, N. Motamedi, D. DiMaio, W. J. Atwood, T. Stehle, The Greater Affinity of JC Polyomavirus Capsid for alpha2,6-Linked Lactoseries Tetrasaccharide c than for Other Sialylated Glycans Is a Major Determinant of Infectivity, Journal of virology, 89 (2015) 6364-6375.

[12] B. Tsai, J. M. Gilbert, T. Stehle, W. Lencer, T. L. Benjamin, T. A. Rapoport, Gangliosides are receptors for murine polyoma virus and SV40, The EMBO journal, 22 (2003) 4346-4355.

[13] U. Neu, S. A. Allen, B. S. Blaum, Y. Liu, M. Frank, A. S. Palma, L. J. Stroh, T. Feizi, T. Peters, W. J. Atwood, T. Stehle, A structure-guided mutation in the major capsid protein retargets BK polyomavirus, PLoS pathogens, 9 (2013) e1003688.

[14] S. Eash, K. Manley, M. Gasparovic, W. Querbes, W. J. Atwood, The human polyomaviruses, Cellular and molecular life sciences: CMLS, 63 (2006) 865-876.

[15] S. Gleiter, H. Lilie, Coupling of antibodies via protein Z on modified polyoma virus-like particles, Protein science: a publication of the Protein Society, 10 (2001) 434-444.

[16] S. Gleiter, H. Lilie, Cell-type specific targeting and gene expression using a variant of polyoma VP1 virus-like particles, Biological chemistry, 384 (2003) 247-255.

[17] Y. Kitai, H. Fukuda, T. Enomoto, Y. Asakawa, T. Suzuki, S. Inouye, H. Handa, Cell selective targeting of a simian virus 40 virus-like particle conjugated to epidermal growth factor, Journal of biotechnology, 155 (2011) 251-256.

[18] S. Thrane, C. M. Janitzek, M. O. Agerbaek, S. B. Ditlev, M. Resende, M. A. Nielsen, T. G. Theander, A. Salanti, A. F. Sander, A Novel Virus-Like Particle Based Vaccine Platform Displaying the Placental Malaria Antigen VAR2CSA, PloS one, 10 (2015) e0143071.

[19] S. Gleiter, K. Stubenrauch, H. Lilie, Changing the surface of a virus shell fusion of an enzyme to polyoma VP1, Protein science: a publication of the Protein Society, 8 (1999) 2562-2569.

[20] U. Schmidt, R. Rudolph, G. Bohm, Binding of external ligands onto an engineered virus capsid, Protein engineering, 14 (2001) 769-774.

[21] K. Tegerstedt, A. V. Franzen, K. Andreasson, J. Joneberg, S. Heidari, T. Ramqvist, T. Dalianis, Murine polyomavirus virus-like particles (VLPs) as vectors for gene and immune therapy and vaccines against viral infections and cancer, Anticancer research, 25 (2005) 2601-2608.

[22] D. Chang, C. Y. Fung, W. C. Ou, P. C. Chao, S. Y. Li, M. Wang, Y. L. Huang, T. Y. Tzeng, R. T. Tsai, Self-assembly of the JC virus major capsid protein, VP1, expressed in insect cells, The Journal of general virology, 78 (Pt 6) (1997) 1435-1439.

[23] C. Goldmann, H. Petry, S. Frye, O. Ast, S. Ebitsch, K. D. Jentsch, F. J. Kaup, F. Weber, C. Trebst, T. Nisslein, G. Hunsmann, T. Weber, W. Luke, Molecular cloning and expression of major structural protein VP1 of the human polyomavirus JC virus: formation of virus-like particles useful for immunological and therapeutic studies, Journal of virology, 73 (1999) 4465-4469.

[24] M. A. Kawano, T. Inoue, H. Tsukamoto, T. Takaya, T. Enomoto, R. U. Takahashi, N. Yokoyama, N. Yamamoto, A. Nakanishi, T. Imai, T. Wada, K. Kataoka, H. Handa, The VP2/VP3 minor capsid protein of simian virus 40 promotes the in vitro assembly of the major capsid protein VP1 into particles, The Journal of biological chemistry, 281 (2006) 10164-10173.

[25] L. Gorelik, C. Reid, M. Testa, M. Brickelmaier, S. Bossolasco, A. Pazzi, A. Bestetti, P. Carmillo, E. Wilson, M. McAuliffe, C. Tonkin, J. P. Carulli, A. Lugovskoy, A. Lazzarin, S. Sunyaev, K. Simon, P. Cinque, Progressive multifocal leukoencephalopathy (PML) development is associated with mutations in JC virus capsid protein VP1 that change its receptor specificity, The Journal of infectious diseases, 204 (2011) 103-114.

[26] R. Komagome, H. Sawa, T. Suzuki, Y. Suzuki, S. Tanaka, W. J. Atwood, K. Nagashima, Oligosaccharides as receptors for JC virus, Journal of virology, 76 (2002) 12992-13000.

[27] A. Ashok, W. J. Atwood, Virus receptors and tropism, Advances in experimental medicine and biology, 577 (2006) 60-72.

[28] M. Ahmad, M. Hirz, H. Pichler, H. Schwab, Protein expression in *Pichia pastoris*: recent achievements and perspectives for heterologous protein production, Applied microbiology and biotechnology, 98 (2014) 5301-5317.

[29] C. L. Young, Z. T. Britton, A. S. Robinson, Recombinant protein expression and purification: a comprehensive review of affinity tags and microbial applications, Biotechnology journal, 7 (2012) 620-634.

[30] S. Maschauer, J. Einsiedel, R. Haubner, C. Hocke, M. Ocker, H. Hubner, T. Kuwert, P. Gmeiner, O. Prante, Labeling and glycosylation of peptides using click chemistry: a general approach to (18)F-glycopeptides as effective imaging probes for positron emission tomography, Angewandte Chemie, 49 (2010) 976-979.

[31] S. S. Shekhawat, I. Ghosh, Split-protein systems: beyond binary protein-protein interactions, Current opinion in chemical biology, 15 (2011) 789-797.

[32] D. Russell, N. J. Oldham, B. G. Davis, Site-selective chemical protein glycosylation protects from autolysis and proteolytic degradation, Carbohydrate research, 344 (2009) 1508-1514.

[33] A. Dondoni, A. Massi, P. Nanni, A. Roda, A new ligation strategy for peptide and protein glycosylation: photoinduced thiol-ene coupling, Chemistry, 15 (2009) 11444-11449.

[34] D. Crich, Mechanism of a chemical glycosylation reaction, Accounts of chemical research, 43 (2010) 1144-1153.

[35] L. Bohe, D. Crich, A propos of glycosyl cations and the mechanism of chemical glycosylation; the current state of the art, Carbohydrate research, 403 (2015) 48-59.

[36] Z. L. Wu, X. Huang, A. J. Burton, K. A. Swift, Glycoprotein labeling with click chemistry (GLCC) and carbohydrate detection, Carbohydrate research, 412 (2015) 1-6.

[37] W. J. Lin, W. Y. Hsu, Pegylation effect of chitosan based polyplex on DNA transfection, Carbohydrate polymers, 120 (2015) 7-14.

[38] S. N. Wang, Y. H. Deng, H. Xu, H. B. Wu, Y. K. Qiu, D. W. Chen, Synthesis of a novel galactosylated lipid and its application to the hepatocyte-selective targeting of liposomal doxorubicin, European journal of pharmaceutics and biopharmaceutics: official journal of Arbeitsgemeinschaft fur Pharmazeutische Verfahrenstechnik e.V, 62 (2006) 32-38.

[39] H. Zhang, Y. Xiao, S. Cui, Y. Zhou, K. Zeng, M. Yan, C. Zhao, Novel Galactosylated Poly(ethylene glycol)-Cholesterol for Liposomes as a Drug Carrier for Hepatocyte-Targeting, Journal of nanoscience and nanotechnology, 15 (2015) 4058-4069.

[40] A. Pagani, M. Vieillevoye, A. Nai, M. Rausa, M. Ladli, C. Lacombe, P. Mayeux, F. Verdier, C. Camaschella, L. Silvestri, Regulation of cell surface transferrin receptor-2 by iron-dependent cleavage and release of a soluble form, Haematologica, 100 (2015) 458-465.

[41] B. Frolund, B. Ebert, U. Kristiansen, T. Liljefors, P. Krogsgaard-Larsen, GABA(A) receptor ligands and their therapeutic potentials, Current topics in medicinal chemistry, 2 (2002) 817-832.

[42] X. Y. Chen, G. Q. Ru, Y. Y. Ma, J. Xie, W. Y. Chen, H. J. Wang, S. B. Wang, L. Li, K. T. Jin, X. L. He, X. Z. Mou, High expression of substance P and its receptor neurokinin-1 receptor in colorectal cancer is associated with tumor progression and prognosis, OncoTargets and therapy, 9 (2016) 3595-3602.

[43] S. S. Rizk, A. Misiura, M. Paduch, A. A. Kossiakoff, Substance P derivatives as versatile tools for specific delivery of various types of biomolecular cargo, Bioconjugate chemistry, 23 (2012) 42-46.

[44] J. F. Peppin, R. B. Raffa, Delta opioid agonists: a concise update on potential therapeutic applications, Journal of clinical pharmacy and therapeutics, 40 (2015) 155-166.

[45] I. S. Zagon, Y. Wu, P. J. McLaughlin, Opioid growth factor and organ development in rat and human embryos, Brain research, 839 (1999) 313-322.

[46] P. J. McLaughlin, I. S. Zagon, J. Skitzki, Human neuroblastoma cell growth in tissue culture is regulated by opioid growth factor, International journal of oncology, 14 (1999) 373-380.

[47] S. W. Jones, R. Christison, K. Bundell, C. J. Voyce, S. M. Brockbank, P. Newham, M. A. Lindsay, Characterisation of cell-penetrating peptide-mediated peptide delivery, British journal of pharmacology, 145 (2005) 1093-1102.

[48] C. M. Dundas, D. Demonte, S. Park, Streptavidin-biotin technology: improvements and innovations in chemical and biological applications, Applied microbiology and biotechnology, 97 (2013) 9343-9353.

[49] E. A. Teunissen, M. de Raad, E. Mastrobattista, Production and biomedical applications of virus-like particles derived from polyomaviruses, Journal of controlled release: official journal of the Controlled Release Society, 172 (2013) 305-321.
[50] A. Abbing, U. K. Blaschke, S. Grein, M. Kretschmar, C. M. Stark, M. J. Thies, J. Walter, M. Weigand, D. C. Woith, J. Hess, C. O. Reiser, Efficient intracellular delivery of a protein and a low molecular weight substance via recombinant polyomavirus-like particles, The Journal of biological chemistry, 279 (2004) 27410-27421.
[51] L. Chen, D. B. Flies, Molecular mechanisms of T cell co-stimulation and co-inhibition, Nature reviews. Immunology, 13 (2013) 227-242.
[52] P. B. Davis, M. J. Cooper, Vectors for airway gene delivery, The AAPS journal, 9 (2007) E11-17.
[53] S. Li, Z. Ma, Nonviral gene therapy, Current gene therapy, 1 (2001) 201-226.
[54] H. Yin, R. L. Kanasty, A. A. Eltoukhy, A. J. Vegas, J. R. Dorkin, D. G. Anderson, Non-viral vectors for gene-based therapy, Nature reviews. Genetics, 15 (2014) 541-555.
[55] D. Fioretti, S. Iurescia, V. M. Fazio, M. Rinaldi, DNA vaccines: developing new strategies against cancer, Journal of biomedicine & biotechnology, 2010 (2010) 174378.
[56] B. Volz, M. Schmidt, K. Heinrich, K. Kapp, M. Schroff, B. Wittig, Design and characterization of the tumor vaccine MGN1601, allogeneic fourfold gene-modified vaccine cells combined with a TLR-9 agonist, Molecular therapy oncolytics, 3 (2016) 15023.
[57] D. B. Hoffmann, K. O. Boker, S. Schneider, E. Eckermann-Felkl, A. Schuder, M. Komrakova, S. Sehmisch, J. Gruber, In Vivo siRNA Delivery Using JC Virus-like Particles Decreases the Expression of RANKL in Rats, Molecular therapy. Nucleic acids, 5 (2016) e298.
[58] X. Li, P. Stuckert, I. Bosch, J. D. Marks, W. A. Marasco, Single-chain antibody-mediated gene delivery into ErbB2-positive human breast cancer cells, Cancer gene therapy, 8 (2001) 555-565.
[59] E. Song, P. Zhu, S. K. Lee, D. Chowdhury, S. Kussman, D. M. Dykxhoorn, Y. Feng, D. Palliser, D. B. Weiner, P. Shankar, W. A. Marasco, J. Lieberman, Antibody mediated in vivo delivery of small interfering RNAs via cell-surface receptors, Nature biotechnology, 23 (2005) 709-717.
[60] F. Nau, Jr., B. Yu, D. Martin, C. D. Nichols, Serotonin 5-HT2A receptor activation blocks TNF-alpha mediated inflammation in vivo, PloS one, 8 (2013) e75426.
[61] A. Millson, A. Suli, L. Hartung, S. Kunitake, A. Bennett, M. G. Nordberg, W. Hanna, C. T. Wittwer, A. Seth, E. Lyon, Comparison of two quantitative polymerase chain reaction methods for detecting HER2/neu amplification, The Journal of molecular diagnostics: JMD, 5 (2003) 184-190.

The invention claimed is:

1. A method of producing a polyomavirus or polyomavirus-derived virus-like particle (VLP) carrying on its surface at least one targeting molecule that binds to a cell of interest, the method comprising the step of contacting the polyomavirus or polyomavirus-derived VLP with (i) the at least one targeting molecule, wherein the at least one targeting molecule is glycosylated with at least one glycosyl residue that is recognised by the polyomavirus or polyomavirus-derived VLP, wherein the at least one glycosyl residue comprises α2,3-, α2,8-, or α2,6-SA; or (ii) a first interaction molecule, wherein the first interaction molecule is glycosylated with at least one glycosyl residue that is recognised by the polyomavirus or polyomavirus-derived VLP; and the at least one targeting molecule, wherein the at least one targeting molecule is conjugated to a second interaction molecule capable of interacting with the first interaction molecule, and wherein the at least one glycosyl residue comprises α2,3-, α2,8-, or α2,6-SA.

2. The method of claim 1, wherein the polyomavirus is the human polyoma JC virus or wherein the VLP is derived from the human polyoma JC virus.

3. The method of claim 1 or 2, wherein the VLP comprises the capsid protein VP1 of the human polyoma JC virus.

4. The method of any one of claims 1 to 3, wherein the glycosyl residue is selected from lactoseries tetrasaccharide c (LSTc), GM1, asialo-GM1, GM2, GD1a, GD1b, GD2, GT1a, GT1b, GM3, GD3, and GQ1b.

5. The method of any one of claims 1 to 4, wherein the at least one targeting molecule is selected from a protein, a peptide, or a carbohydrate.

6. The method of claim 5, wherein the at least one targeting molecule is a protein selected from an antibody, transferrin, epidermal growth factor (EGF) family members, a cytokine, a partial viral glycoprotein, CD9, CD63, var2csa, insulin or a ligand for GABA.

7. The method of claim 5, wherein the at least one targeting molecule is a peptide selected from substance-P, an opioid or cell-penetrating peptides.

8. The method of any one of claims 1 to 7, wherein the first and second interaction molecules are Avidin and Biotin, Streptavidin and Biotin, or NeutrAvidin and Biotin.

9. The method of any one of claims 1 to 8, wherein the virus or VLP further comprises one or more cargo molecule(s) within the virus or VLP.

10. The method of any one of claims 1 to 9, wherein the virus or VLP further comprises additional heterologous molecules on the surface of the virus or VLP.

11. A polyomavirus or polyomavirus-derived virus-like particle (VLP), wherein the virus or VLP carries on its surface at least one targeting molecule that binds to a cell of interest, and wherein the at least one targeting molecule has been bound to the surface of the virus or VLP via:

(i) a glycosylation of the at least one targeting molecule with at least one glycosyl residue, wherein said at least one glycosyl residue is recognised and bound by the polyomavirus or polyomavirus-derived VLP, and wherein the at least one glycosyl residue comprises α2,3-, α2,8-, or α2,6-SA; or (ii) the interaction between at least two interaction molecules, wherein a first interaction molecule is glycosylated with at least one glycosyl residue, wherein said at least one glycosyl residue is recognised and bound by the polyomavirus or polyomavirus-derived VLP; and wherein the at least one targeting molecule is conjugated to a second interaction molecule capable of interacting with the first interaction molecule, and wherein the at least one glycosyl residue comprises α2,-3, α2,8-, or α2,6-SA.

12. The polyomavirus or polyomavirus-derived VLP of claim 11, wherein the virus or VLP is obtained or obtainable by the method of any one of claims 1 to 10.

13. A composition comprising the polyomavirus or polyomavirus-derived VLP of claim 11 or 12.

14. The polyomavirus or polyomavirus-derived VLP of claim 11 or 12 or the composition of claim 13 for use as a medicament.

15. A kit comprising the polyomavirus or polyomavirus-derived virus-like particle (VLP) of claim 11 or 12, or the composition of claim 13.

* * * * *